(12) United States Patent
Schwartz et al.

(10) Patent No.: US 8,629,233 B2
(45) Date of Patent: Jan. 14, 2014

(54) PHENYL ESTER SIDE CHAINS TO INCREASE POLYMER RESORPTIVITY

(75) Inventors: Arthur Schwartz, East Windsor, NJ (US); Satish Pulapura, Bridgewater, NJ (US); Sarita Nethula, Somerset, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 692 days.

(21) Appl. No.: 12/641,996

(22) Filed: Dec. 18, 2009

(65) Prior Publication Data

US 2010/0167992 A1 Jul. 1, 2010

Related U.S. Application Data

(63) Continuation of application No. PCT/US2008/067715, filed on Jun. 20, 2008.

(60) Provisional application No. 60/945,508, filed on Jun. 21, 2007.

(51) Int. Cl.
*C08G 69/44* (2006.01)

(52) U.S. Cl.
USPC .......................................................... 528/203

(58) Field of Classification Search
None
See application file for complete search history.

(56) References Cited

U.S. PATENT DOCUMENTS

| | | | |
|---|---|---|---|
| 3,803,120 A * | 4/1974 | Felix | ............................ 530/331 |
| 6,120,491 A | 9/2000 | Kohn et al. | |
| 2004/0170685 A1 | 9/2004 | Carpenter et al. | |
| 2005/0036978 A1 | 2/2005 | Kozlowski | |
| 2005/0165203 A1 | 7/2005 | Kohn et al. | |
| 2006/0110743 A1 | 5/2006 | Konishi et al. | |

FOREIGN PATENT DOCUMENTS

| | | |
|---|---|---|
| JP | 2000501139 A | 2/2000 |
| JP | 2001514618 A | 9/2001 |
| JP | 2006520217 A | 9/2006 |
| WO | 9719996 A1 | 6/1997 |
| WO | 9836013 A1 | 8/1998 |
| WO | WO 2007/056134 A2 | 5/2007 |

OTHER PUBLICATIONS

Young, "International Search Report" from PCT/US2008/067715, 4 pages, United Sates Patent and Trademark Office, Alexandria, Virginia (mailed Sep. 24, 2008.

Young, "Written Opinion of the International Searching Authority" from PCT/US2008/067715, 6 pages, United Sates Patent and Trademark Office, Alexandria, Virginia (mailed Sep. 24, 2008).

Japanese Office Action dated Feb. 26, 2013 for Application No. 2010/513454.

* cited by examiner

*Primary Examiner* — Thomas Heard
(74) *Attorney, Agent, or Firm* — Lerner, David, Littenberg, Krumholz & Mentlik, LLP

(57) ABSTRACT

The present invention relates to polymers modified to increase their resorbability. In particular, the polymers of the invention have phenyl ester side chains which are good leaving groups and which thereby increase the resorption rate of the polymer relative to the same polymer, for example, bearing a comparable amount of an alkyl ester side chain. Such polymers are generally water insoluble, but when modified are able to solublize drugs and upon degradation and resorption, release those in a physiological environment in a controlled and/or sustained manner.

16 Claims, 3 Drawing Sheets

PHENYL ESTER SIDE CHAINS TO INCREASE POLYMER RESORPTIVITY

CROSS-REFERENCE TO RELATED APPLICATION

This application is a continuation of PCT Application Number PCT/US2008/067715 filed Jun. 20, 2008 which claims priority to U.S. Provisional Application Ser. No. 60/945,508 filed Jun. 21, 2007 the disclosures of which are each herein incorporated by reference in their entirety for all purposes.

BACKGROUND OF THE INVENTION

Biocompatible, biodegradable polymers have diverse medical uses and often provide controlled or sustained drug delivery—whether from pharmaceutical compositions, as medical devices, or when used in conjunction with medical devices. Pharmaceutical compositions can be designed for many, if not all known medicinal delivery routes, including oral, intramuscular, subcutaneous, intraarticular, intranasal, topical, or other delivery route using biocompatible polymers. Such polymers are also used for controlled drug delivery in conjunction with medical devices and prostheses. For example, biocompatible polymers and drugs have been applied as coatings to implantable medical devices to provide controlled or sustained drug release. Applying a polymer coating provides one strategy to change the physicomechanical properties of the underlying device and can improve handling during surgical procedures. Additionally, medical devices, e.g., surgical meshes, bone prostheses and surgical closure devices, can be formed from or include a component with biocompatible polymers. Such devices can also have drugs incorporated at the time of manufacture and or later by post-manufacture coating or impregnation.

The profile of drug release depends on many factors, including polymer properties, drug properties, delivery route, delivery mode, other components that may be present or relevant such as individual metabolism, enzymatic action, degree of vascularization and more. Moreover, there are often manufacturing and compatibility challenges such as drug solubility or temperature sensitivity, that arise when selecting a polymer-drug system or formulation that provides a desired release profile yet remains biocompatible without untoward side effects in a subject. Given the diversity of polymers, drugs and medical applications, there is always a need for new polymers to provide polymer-drug combinations that can be manipulated to suit the medical condition or need. The present invention addresses the need for biocompatible, biodegradable and resorbable polymers that can be used to create medicines or to use with, in, on or as part of medical devices to provide the clinician with greater options for drug delivery, including for controlled, sustained or defined periods of drug release.

Finally, use of the polymers of the present invention provide a novel method to generate free carboxylic acid groups during in vivo use (rather than at the time of polymer synthesis and have certain synthetic advantages), and thus provide polymers with a greater range of chemical properties as well as the greater drug delivery capabilities.

SUMMARY OF THE INVENTION

The present invention is directed to resorbable polymers that are biocompatible, biodegradable polymers capable of resorption under physiological conditions. In one embodiment, the polymers of the invention comprise one or more monomer units represented by Formula I:

wherein "Monomer" represents the repeating unit of a biocompatible, biodegradable polymer capable of resorption under physiological conditions and has a phenyl ester side chain such that R' is phenyl-R.

In particular, "Monomer" represents the repeating unit of a biocompatible, biodegradable polymer capable of resorption under physiological conditions;

R' is phenyl-R, wherein from zero to five R substituents are present at any position on the phenyl ring, and each R is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; —$(R_2)_rO((CR_3R_4)_aO)_s$—$R_5$; —$O((CR_3R_4)_aO)_s$—$R_5$; —$C(O)$—$R_5$; —$(R_2)_bC(O)$—$YR_6$; a protected hydroxyl group; a protected amino group or a protected carboxylic acid group;

Y is —O— or —NH—;

each $R_2$ is independently linear or branched, lower alkylene or lower alkenylene;

each $R_3$ and $R_4$ is independently hydrogen, or linear or branched lower alkyl;

each $R_5$ is independently linear or branched, substituted or unsubstituted, saturated or unsaturated alkyl;

each $R_6$ is hydrogen; saturated or unsaturated alkyl, aryl or alkylaryl having from 1 to 20 carbon atoms; or —$(R_2)_rO((CR_3R_4)_aO)_s$—$R_5$;

each a is independently 1 to 4;

each b is independently zero or one;

each r is independently 1 to 4; and each s is independently 1 to 5000.

In particular embodiments, the polymers of the invention comprise from at least about 0.1% to 100% of Monomer and thus include copolymers and homopolymers.

In another embodiment, the polymers of the invention comprise one or more diphenol monomer units represented by Formula II:

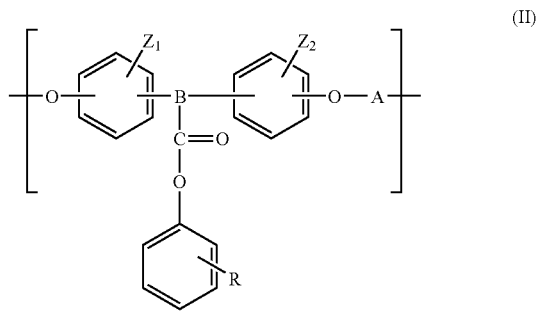

These diphenol monomer units provide biocompatible, biodegradable polymers with pendant phenyl ester side chains, which polymers are capable of resorption under physiological conditions In particular, A is —C(O)—, —C(O)—R$_1$—C(O)—, —C(=NH)—, —C(O)—NH—R$_1$—NH—C(O)— or —C(S)—;

B is a trivalent, linear or branched, substituted or unsubstituted alkyl, alkenyl, aryl or alkylaryl moiety having 1-20 carbon atoms, or is

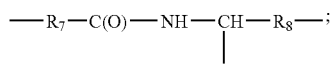

each backbone aromatic ring has from zero to four Z$_1$ or Z$_2$ substituents, each of which is independently selected from the group consisting of halide, lower alkyl, alkoxy, nitro, alkylether, a protected hydroxyl group, a protected amino group and a protected carboxylic acid group;

the pendant phenyl ring has from zero to five R substituents at any position on the phenyl ring, and each R is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; —(R$_2$)$_r$O((CR$_3$R$_4$)$_a$O)$_s$—R$_5$; —O((CR$_3$R$_4$)$_a$O)$_s$—R$_5$; —C(O)—R$_5$; —(R$_2$)$_b$C(O)—YR$_6$; a protected hydroxyl group; a protected amino group or a protected carboxylic acid group;

R$_1$ is, independently, a divalent, linear or branched, substituted or unsubstituted alkyl, alkenyl, alkynyl, aryl, alkylaryl, alkylene oxide or arylene oxide moiety having from 1 to 30 carbon atoms; —(R$_2$)$_r$O((CR$_3$R$_4$)$_a$O)$_s$(R$_2$)$_r$; or —(R$_2$)$_r$CO$_2$((CR$_3$R$_4$)$_a$O)$_s$CO(R$_2$)$_r$;

each R$_2$ is independently linear, lower alkylene or lower alkenylene;

each R$_3$ and R$_4$ is independently hydrogen, or linear or branched lower alkyl;

R$_5$ is independently linear or branched, substituted or unsubstituted, saturated or unsaturated alkyl;

R$_6$ is hydrogen; saturated or unsaturated alkyl, aryl or alkylaryl having from 1 to 20 carbon atoms; or —(R$_2$)$_r$O((CR$_3$R$_4$)$_a$O)$_s$—R$_5$;

R$_7$ is independently a bond, or linear or branched, substituted or unsubstituted alkyl, alkenyl or alkynyl having from 1 to 20 carbon atoms, and when substituted, the substituent can be, but is not limited to, —X, —CX$_3$, —CHX$_2$, —CH$_2$X, —NHR$_9$, or —NHC(O)R$_{10}$;

R$_8$ is independently a bond or linear or branched, substituted or unsubstituted alkyl, alkenyl or alkynyl having from 1 to 20 carbon atoms, and when substituted, the substituent can be, but is not limited to, —X, —CX$_3$, —CHX$_2$, —CH$_2$X, —NHR$_9$, or —NHC(O)R$_{10}$;

R$_9$ is a linear or branched, substituted or unsubstituted, saturated or unsaturated alkyl, aryl or alkylaryl group or an amino protecting group;

R$_{10}$ is a linear or branched alkyl, aryl or alkylaryl group;

X is a halogen;

Y is —O— or —NH—;

each a is independently 1 to 4;

each b is independently zero or one;

each r is independently 1 to 4; and each s is independently 1 to 5000.

In some embodiments, the polymers of the invention comprise from at least about 0.1% to 100% of these diphenol monomer units.

In other embodiments, the polymers have A as —C(O)—R$_1$—C(O) and B as

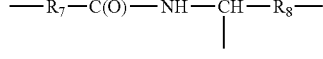

wherein R$_1$ is methylene, ethylene or n-propylene, and R$_7$ and R$_8$ are preferably a bond, methylene or ethylene.

When the polymers of the invention are copolymers containing a Monomer or a diphenol monomer unit of Formula II, then the other monomer units of those copolymers can be nearly the same as the Monomer or the diphenol monomer unit of Formula II, except that the phenyl ester moiety can be replaced by hydrogen (to form a free COOH group), by another ester class such as alkyl esters, alkylaryl esters, or esters with alkylene oxide chains or ether chains, by amides or by another compatible functional group. Further, in addition to the foregoing changes or instead of the foregoing changes, the other monomer units can be similar to the Monomer or the diphenol monomer units of Formula II but have variability among the different substituents, i.e., differences can reside at any of A, B, R$_1$-R$_{10}$, X, Y or the other variables of Formulas I and II. Finally, the other monomer units in the copolymer can be substantially different provided such moieties preserve the properties of the polymer and are capable of copolymerizing with the Monomer or the diphenol monomeric unit of Formula II.

A further aspect of the invention is directed to polymers of the invention blended with one or more second polymers. The second polymers are also biocompatible but can be biodegradable, resorbable or stable as needed for the particular use, whether formed into a device, on a device (as by coating, a film or the like), as a pharmaceutical composition to manipulate drug elution profile and the like. Particularly useful second polymers, especially for fully resorbable products, include polyethylene glycol (PEG), poly(D,L-lactide) (PLA), polyglycolic acid [polyglycolide (PGA)], poly(D,L-lactide-co-glycolide) (PLGA) and other diphenol-derived or tyrosine-derived polyarylates. The polymers blends of the invention can further include one or more drugs.

In another aspect of the invention, the polymers and blends of the invention are formulated into pharmaceutical compositions comprising one or more drugs, and optionally, one or more pharmaceutically-acceptable carriers. Such drugs include, but are not limited to, antimicrobial agents, anesthetics, anti-inflammatory agents, anti-scarring agents, growth factors and anti-fibrotic agents.

In a further aspect, the invention is directed to a medical device comprising one or more of the polymers or blends of the invention, with or without one or more drugs. Moreover, the medical device can be coated with one or more of the polymers or blends of the invention. Such devices include but are not limited to, implantable or insertable devices such as stents; surgical meshes; coverings, pouches, pockets, bags and the likes for devices; wound closure adjuncts and any type of catheter. Coatings, when present, can be on any surface of the device, as a partial or full coating, and can be single or multi-layered, using the present polymers and blends or using layers made from other biocompatible polymers.

Yet another aspect of the invention provides monomeric compounds represented by Formula III or IV

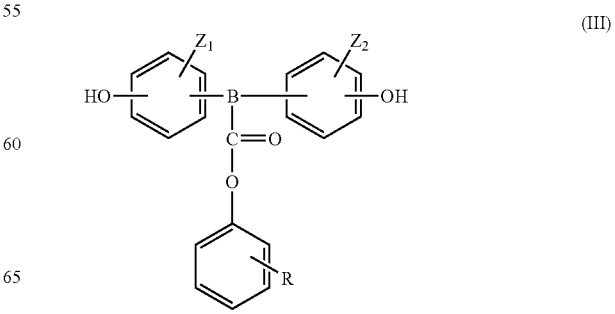

-continued

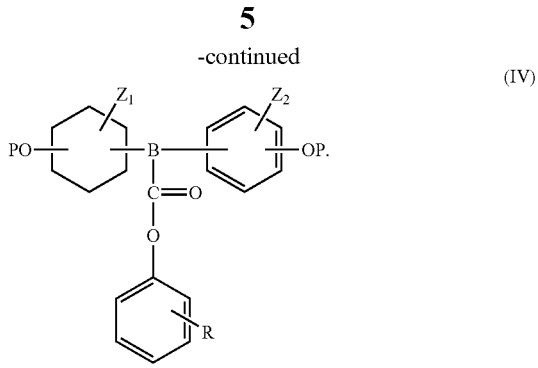

(IV)

These monomeric compounds have phenyl esters moieties and can be used in the synthesis of the polymers of the invention, namely the biocompatible, biodegradable polymers capable of resorption under physiological conditions. Compounds of Formula III have free hydroxyls and those of Formula IV have hydroxyl protecting groups (P). The other substituents are as described above for the diphenol monomeric units of Formula II. In a preferred embodiment, the monomeric compounds of the invention are those wherein B is

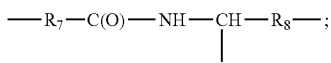

In a still further aspect, the instant invention provides methods of treating a disorder or condition in a patient by implanting a medical device of the invention in a patient, with or without one or more drug(s). Implantable medical devices of the invention can be used to treat or ameliorate a cardiovascular disorder, a neurological disorder, a hernia or hernia-related disorder, an ophthalmic condition, or to effectuate an anatomical repair, reconstruction, replacement or augmentation of a body part, limb, tissue or organ of a patient. For example, these methods can ameliorate the morbidities associated with implantation of a comparable untreated medical device.

Such morbidities include scarring, pain and infection.

DETAILED DESCRIPTION OF THE INVENTION

Figure 1:
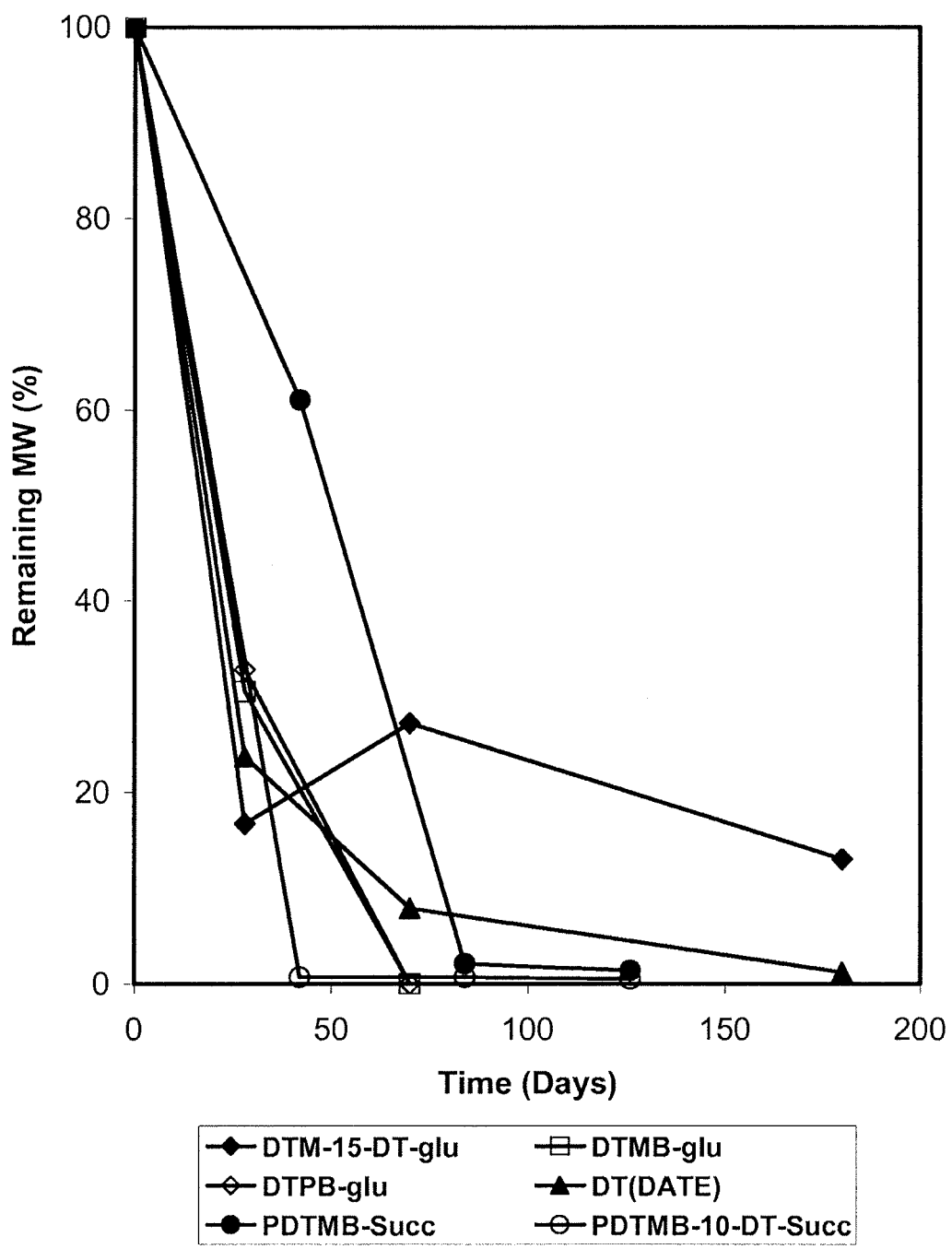
FIG. 1 graphically illustrates the change in polymer molecular weight in vivo as a function of time for (♦) poly (DTM-15-DT glutarate), (◊) poly(DTPB glutarate), (●) poly(DTMB succinate), (□) poly(DTMB glutarate), (▲) poly(DT(DATE) glutarate) and (○) poly(DTMB-10-DT succinate).

In most embodiments, the present invention relates to medically-relevant, biodegradable polymers with carboxylic acid side chains protected by facile leaving groups. In particular, these leaving groups are phenyl esters, which upon cleavage in situ, generate free carboxylic acid groups on the polymer to thereby increase polymer degradation and resorbability. The present invention is also directed to pharmaceutical compositions comprising the polymers of the invention and one or more drugs as well as medical devices made from or coated with a polymer of the invention, and optionally, with one or more drugs.

DEFINITIONS AND ABBREVIATIONS

The compounds herein described may have asymmetric centers. All chiral, diastereomeric, and racemic forms are included in the present invention. Geometric isomers of olefins and the like can also be present in the compounds described herein, and all such stable isomers are contemplated in the present invention.

By "stable compound" or "stable structure" is meant herein a compound or molecule that is sufficiently robust to survive isolation to a useful degree of purity from a reaction mixture, and for formulation into or use into an efficacious therapeutic agent.

As used herein, unless otherwise clear from the context, "alkyl" means both branched- and straight-chain, saturated aliphatic hydrocarbon groups having the specified number of carbon atoms. Straight and linear are used interchangeably. As used herein "lower alkyl" means an alkyl group having 1 to 6 carbon atoms. When substituted, the substituents can include halide, alkyl, alkoxy, hydroxy, amino, cyan, nitro, trifluoromethyl, trifluoroethyl, additional substituents as described herein, and the like compatible with the properties and synthesis of the molecules of the invention.

As used herein, "alkenyl" means hydrocarbon chains of either a straight or branched configuration having one or more unsaturated carbon-carbon double bonds, such as ethenyl, propenyl, and the like. "Lower alkenyl" is an alkenyl group having 2 to 6 carbon atoms. As used herein, "alkynyl" means hydrocarbon chains of either a straight or branched configuration having one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl means having from 1-20 carbon atoms. Alkylene and alkenylene groups are alkyl groups and alkenyl groups, respectively, which are divalent. When substituted, the substituents can include halide, alkyl, alkoxy, hydroxy, amino, cyano, nitro, trifluoromethyl, trifluoroethyl, additional substituents as described herein, and the like compatible with the properties and synthesis of the molecules of the invention.

As used herein, "saturated or unsaturated alkyl" refers to any of an alkyl group an alkenyl group or an alkynyl group, having any degree of saturation, i.e., completely saturated (as in alkyl), one or more double bonds (as in alkenyl) or one or more triple bonds (as in alkynyl).

Examples of alkyl groups include but are not limited to, methyl, ethyl, n-propyl, isopropyl, n-butyl, isobutyl, t-butyl, pentyl, hexyl, n-heptyl, n-octyl, isooctyl, nonyl, decyl, and the like; alkylene and alkenylene groups include but are not limited to, methylene, ethylene, propylenes, propenylene, butylenes, butadiene, pentene, n-hexene, isohexene, n-heptene, n-octene, isooctene, nonene, decene, and the like. Those of ordinary skill in the art are familiar with numerous linear and branched hydrocarbon groups. Alkynyl groups include ethynyl and propynyl groups.

As used herein, "aryl" means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. When substituted, the substituents can include halide, alkyl, alkoxy, hydroxy, amino, cyano, nitro, trifluoromethyl, trifluoroethyl, additional substituents as described herein, and the like compatible with the properties and synthesis of the molecules of the invention.

As used herein, the term "heteroaryl" means a stable 5- to 10-membered monocyclic or bicyclic heterocyclic ring which is aromatic, and which consists of carbon atoms and from 1 to 3 heteroatoms selected from the group consisting of N, O and S and wherein the nitrogen can optionally be quaternized, and including any bicyclic group in which any of the above-defined heteroaryl rings is fused to a benzene ring. The heteroaryl ring may be attached to its pendant group at any heteroatom or carbon atom which results in a stable structure. The presence of substitution on the heteroaryl group is optional and can be on a carbon atom, a nitrogen atom or other heteroatom if the resulting compound is stable and all the valencies of the atoms have been satisfied. When present, the substituents of the substituted heteroaryl groups are the same as for the substituted aryl groups and also include alkylammonium salts when the substituent is an alkyl group attached to the nitrogen atom of the heteroaryl ring. These quarternized ammonium salts include halides, hydrohalides, sulfates, methosulfates, methanesulfates, toluenesulfates, nitrates, phosphates, maleates, acetates, lactates or any other pharmaceutically acceptable salt. Examples of heteroaryl groups include, but are not limited to, pyridyl, pyrimidinyl, furanyl, thienyl, pyrrolyl, pyrazolyl, imidazolyl, tetrazolyl, benzofuranyl, benzothienyl, indolyl, indolenyl, quinolinyl, isoquinolinyl and benzimidazolyl.

As used herein, "alkylaryl" refers to an aryl group attached to an alkyl group, which in turn is the attachment point of the substituent. The aryl group of this moiety can optionally be substituted in accordance with the definitions herein. For example, a benzyl ester represents an alkylaryl moiety in which the methylene attached on the phenyl ring is bonded to the oxygen of the ester. In contrast, for phenyl esters, the phenyl ring is directly bonded to the oxygen of the ester.

The term "substituted" as used herein means that one or more hydrogens on the designated atom are replaced with a selection from the indicated groups, provided that the designated atom's normal valency is not exceeded, and that the substitution results in a stable compound. If no substituent is indicated then the valency is filled with a hydrogen atom. The substituents of the invention can include, as indicated, halide (also referred to as halo), hydroxy, alkyl, alkoxy, amino, cyano, nitro, trifluoromethyl, aryl, heteroaryl, monoalkylamino, dialkylamino, trialkylammonium and salts thereof, carbamoyl, acylamino, arylcarbonylamino, alkoxycarbonylamino, formamido, guanidino, ureido, sulfamyl, and alkylsulfonamido. These groups can be substituents for alkyl, alkenyl, alkynyl, cycloalkyl, aryl, aralkyl, heteroaryl and heteroaralkyl groups as indicated In accordance with various embodiments of the invention and provided the presence of the substituent is compatible with the properties and synthesis of the molecules of the invention.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted.

A "halide" or a "halo" group is a halogen atom, and includes fluoro, chloro, bromo and iodo groups. The term "alkoxy" refers to an alkyl group having at least one oxygen substituent represented by R—O—.

Examples of poly(alkylene glycols) include, but are not limited to, poly(ethylene oxide)(PEG), poly(propylene glycol)(PPG), poly(tetramethylene glycol), and any derivatives, analogs, homologues, congeners, salts, copolymers and combinations thereof. In some embodiments, the poly(alkylene glycol) is PEG.

As used herein, "therapeutically-effective amount" refers to that amount of a drug or bioactive agent necessary to administer to a host to achieve a desired therapeutic effect in treating, ameliorating or preventing a disease or condition. For example, a therapeutically-effective amount can be that amount to provide antimicrobial activity, pain relief, anti-inflammatory activity, antifibrotic activity, anti-tumor or cancer activity and the like associated with the particular drug or biological agent in use. Therepeutically-effective amounts for known drugs are available in the literature or can be determined, for new or known drugs, using art known methods, techniques and standards.

As used herein, "phainiaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfates, toluenesulfonates, nitrates, phosphates, maleates, acetates, lactates and the like. Pharmaceutically-acceptable salts of the compounds of the invention can be prepared by methods know to those of skill in the art.

Abbreviations used herein for naming polymers and the subunits thereof include B, 4-hydroxybenzoic acid; Bn or Bz, benzyl; D or DAT, desaminotyrosine or desaminotyrosyl; DATE, desaminotyrosine ethyl ester; dig, diglycolate; E or Et, ethyl; glu, glutarate; M or Me, methyl; MB, methylparaben; PB, propyl paraben; PEG, polyethylene glycol; succ, succinate; and T, tyrosine.

The nomenclature for the polymers based on diphenol monomer units have two part names. The first part identifies the diphenol moiety and the second part (the A group) identifies the group with which the diphenol moiety is copolymerized. The names are written in the form poly(diphenol diacid), poly(diphenol carbonate), poly(diphenol iminocarbonate), etc.

The diphenol moiety is generally named for its three components, the two aromatic ring moieties and the tyrosine ester moiety. For example, DTE is desaminotyrosyl-tyrosine ethyl ester; DTBn is desaminotyrosyl-tyrosine benzyl ester. When a free acid is present (rather than an ester), the name for a third component is omitted. Thus, DT is the corresponding free acid form, namely desaminotyrosyl-tyrosine. Also for example, DT(DATE) is the desaminotyrosine ethyl ester (DATE) as the ester on the tyrosine of DT. For a paraben, the diphenol monomer desaminotyrosyl-tyrosine methyl paraben is abbreviated as DTMB; the corresponding propylparaben is DTPB.

The second part of the name identifies the group with which the diphenol moiety is polymerized, such as the diacid, the carbonate, the iminocarbonate and the like. Hence, specific examples include poly(DTE glutarate), poly(DTPB succinate), poly(DTBn carbonate) and the like.

If a mixture of diphenol moieties or of copolymerized groups (such as two diacids) are present in the polymer, then that part of name may includes the designation "co" or may have a hyphen, along with an indication of percentage of one of the two moieties. For example, poly(DTE-co-10-DT succinate) and poly(DTE-10-DT succinate) are used interchangeably to mean a polymer made by copolymerizing a mixture of 90% desaminotyrosyl-tyrosine ethyl ester and 10% desaminotyrosyl-tyrosine with the diacid succinate. An example of a mixed diacid is poly(DTMB PEG-bis-succinate-50-adipate).

Polymer Description

The present invention relates to biocompatible, biodegradable polymers comprising monomer units with pendant phenyl ester (PE) groups, i.e., PE side chains relative to the polymer backbone. When those PE groups are cleaved, removed, degraded or otherwise released from the polymer in vitro, in vivo, in situ (i.e., under physiological conditions), the result is an increase in the free acid content of the polymer, a significant increase in hydrophilicity and an increase in the rate of degradation of the polymer backbone. Without wishing to be bound by a mechanism, when the polymer is driven to breakdown more quickly into more water-soluble constituents, the result is faster resorption. Hence, the present invention is directed to resorbable polymers having pendant phenyl esters.

A biocompatible polymer is a polymer which is compatible with living tissue or a living system and is acceptable for use in or by animals or humans. Thus, a biocompatible polymer does not cause physiological harm to any significant or unacceptable degree, does not cause any or any significant amount of inflammation or immunological reaction, and is not toxic or injurious to the living tissue or system. For example, a biocompatible polymer can be ingested, implanted, placed on or otherwise used in a living subject or tissue without untoward effects.

As used herein, a "biodegradable polymer" is a biocompatible polymer that is hydrolytically labile, oxidatively labile, or susceptible to enzymatic action, or any combination thereof, which action leads to the breakdown, whether partial or complete, of the polymer. It should be understood that polymers which are biodegradable have variable resorption times, which can depend, for example, on the nature and size of the breakdown products.

As used herein a "resorbable polymer," is a biocompatible, biodegradable, polymer (1) with repeating backbone units that are chemically unstable under physiological conditions, i.e., in the presence of water, enzymes or other cellular processes, that is, the polymer is biodegradable, (2) whose degradation products are capable of being taken up and/or assimilated in vivo or under physiological conditions by any mechanism (including by absorption, solubilization, capillary action, osmosis, chemical action, enzymatic action, cellular action, dissolution, erosion and the like or any combination of these processes) in a subject on a physiologically-relevant time scale consonant with the intended use of the polymer, and (3) when modified to have pendant PE groups, those PE groups are facile leaving groups which when removed increase the free acid content of the polymer and thereby increase its hydrophilicity, increase the rate of degradation of the polymer backbone and increase the resorption time of the polymer relative to the same polymer having a comparable amount of pendant PE groups present as pendant aliphatic esters.

Resorbable polymers contain cleavable backbone bonds, that when broken, produce smaller water soluble fragments, which themselves may be polymeric or monomeric. These smaller fragments are or can be (as needed) further degraded to a size that can be engulfed by a macrophage, processed by a cell or otherwise removed from the cellular milieu or tissues at the physiological site of use, resulting in complete or substantially complete resorption of the polymer in a specified time.

When resorbable polymers become completely or substantially resorbed, then the polymer (but not necessarily the monomeric repeating units thereof or smaller polymeric fragments thereof) is no longer present or detectable in the subject. For example, if the polymer is a coating on an implanted medical device, the polymer would no longer be present on or detectable on the device after resorption. Similarly, if the polymer is formed into a medical device (e.g., suture material, a staple, a device covering, an implant, a plug, a drug or vaccine carrier), then the device is no longer present or detectable at the physiological site of use. Without wishing to be bound, one can describe this process as conversion of a water-insoluble polymer into water soluble components or subunits by break down into its components with concomitant elimination or excretion.

The time scale of resorption depends upon the intended use and the polymers of the invention can be manipulated to provide for rapid resorption, e.g., within a few days, to longer periods, such as weeks or months, under physiological conditions. Medically-relevant time periods include, e.g., from 1-30 days and from 1 to 24 months, as well as all time in between such as 5 days, 1-6 weeks, 2, 3, 4, 6 or months and the like.

Accordingly, resorbable polymers of the invention include, but are not limited to, polyesters, polycarbonates, polyarylates, polyamides, polyesteramides, polyurethanes, polyethers, polyphosphoesters, polyiminocarbonates, polyureas, polyphosphates, polyhydrazides, polyanhydrides, and polyphosphazenes which have pendant phenyl ester groups.

Examples of biocompatible polymers that degrade hydrolytically, include, but are not limited to, polyesters, polycarbonates, polyarylates, polyesteramides, polyurethanes, polyethers, polyphosphoesters, polyiminocarbonates, polyphosphates, and polyanhydrides. Examples of biocompatible polymers that can be degraded enzymatically include, but are not limited to, polyesters, polyamides, polyesteramides and polyphosphates.

Accordingly, certain embodiments of the invention are directed to polymers comprising monomers represented by the formula (I):

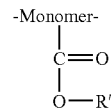

wherein

"Monomer" represents the repeating unit of a biocompatible, biodegradable polymer capable of resorption under physiological conditions;

R' is phenyl-R, wherein from zero to five R substituents are present at any position on the phenyl ring, and each R is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; —$(R_2)_rO((CR_3R_4)_aO)_s$—$R_5$; —$O((CR_3R_4)_aO)_s$—$R_5$; —$C(O)$—$R_5$; —$(R_2)_bC(O)$—$YR_6$; a protected hydroxyl group; a protected amino group or a protected carboxylic acid group;

Y is —O— or —NH—;

each $R_2$ is independently linear or branched, lower alkylene or lower alkenylene;

each $R_3$ and $R_4$ is independently hydrogen, or linear or branched lower alkyl;

each $R_5$ is independently linear or branched, substituted or unsubstituted, saturated or unsaturated alkyl;

each $R_6$ is hydrogen; saturated or unsaturated alkyl, aryl or alkylaryl having from 1 to 20 carbon atoms; or —$(R_2)_rO((CR_3R_4)_aO)_s$—$R_5$;

each a is independently 1 to 4;
each b is independently zero or one;
each r is independently 1 to 4; and
each s is independently 1 to 5000.

The substituents of the Monomer unit of the polymers comprise the backbones, for example, of polyesters, polycarbonates, polyarylates, polyamides, polyesteramides, polyurethanes, polyethers, polyphosphoesters, polyiminocarbonates, polyureas, polyphosphates, polyhydrazides, polyanhydrides, polyphosphazenes and the like.

In general, these polymers contain from at least about 0.1% to 100% of monomer units with the above-defined phenyl ester group.

In another embodiment, the invention is directed to polymers comprising one or more diphenol monomer units represented by the Formula (II)

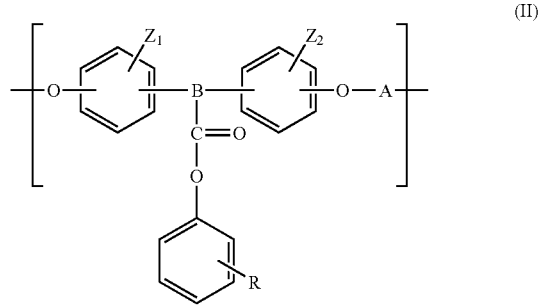

wherein
A is —C(O)—, —C(O)—$R_1$—C(O)—, —C(=NH)—, —C(O)—NH—$R_1$—NH—C(O)— or —C(S)—;
B is a trivalent, linear or branched, substituted or unsubstituted alkyl, alkenyl, aryl or alkylaryl moiety having 1-20 carbon atoms, or is

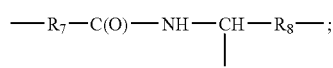

each backbone aromatic ring has from zero to four $Z_1$ or $Z_2$ substituents, each of which is independently selected from the group consisting of halide, lower alkyl, alkoxy, nitro, alkylether, a protected hydroxyl group, a protected amino group and a protected carboxylic acid group;

the pendant phenyl ring has from zero to five R substituents at any position on the phenyl ring, and each R is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; —$(R_2)_rO((CR_3R_4)_aO)_s$—$R_5$; —C(O)—$R_5$; —$(R_2)_bC(O)$—$YR_6$; a protected hydroxyl group; a protected amino group or a protected carboxylic acid group;

$R_1$ is, independently, a divalent, linear or branched, substituted or unsubstituted alkyl, alkenyl, alkynyl, aryl, alkylaryl, alkylene oxide or arylene oxide moiety having from 1 to 30 carbon atoms; —$(R_2)_rO((CR_3R_4)_aO)_s(R_2)_r$; or —$(R_2)_rCO_2((CR_3R_4)_aO)_sCO(R_2)_r$;

each $R_2$ is independently linear or branched, lower alkylene or lower alkenylene;

each $R_3$ and $R_4$ is independently hydrogen, or linear or branched lower alkyl;

$R_5$ is independently linear or branched, substituted or unsubstituted, saturated or unsaturated alkyl;

$R_6$ is hydrogen; saturated or unsaturated alkyl, aryl or alkylaryl having from 1 to 20 carbon atoms; or —$(R_2)_rO((CR_3R_4)_aO)_s$—$R_5$;

$R_7$ is independently a bond, or linear or branched, substituted or unsubstituted alkyl, alkenyl or alkynyl having from 1 to 20 carbon atoms, and when substituted, the substituent can be, but is not limited to, —X, —$CX_3$, —$CHX_2$, —$CH_2X$, —$NHR_9$, or —$NHC(O)R_{10}$;

$R_8$ is independently a bond or linear or branched, substituted or unsubstituted alkyl, alkenyl or alkynyl having from 1 to 20 carbon atoms, and when substituted, the substituent can be, but is not limited to, —X, —$CX_3$, —$CHX_2$, —$CH_2X$, —$NHR_9$, or —$NHC(O)R_{10}$;

$R_9$ is a linear or branched, substituted or unsubstituted, saturated or unsaturated alkyl, aryl or alkylaryl group or an amino protecting group;

$R_{10}$ is a linear or branched alkyl, aryl or alkylaryl group;
X is a halogen;
Y is O or NH;
each a is independently 1 to 4;
each b is independently zero or one;
each r is independently 1 to 4; and
each s is independently 1 to 5000.

These polymers of the invention can be homopolymers or copolymers. When the polymers are copolymers, they contain from at least about 0.1% to 100% of the diphenol monomer units, from at least about 1%, 2%, 3%, 4%, 5%, 6%, 8%, 10%, 12% to about 30%, 40%, 50%, 60%, 75%, 90%, 95% or 99% in any combination of ranges. In certain embodiments, the range of diphenol monomer units with phenyl esters (i.e., those represented by Formula II) in the polymer is from about 5 to about 50%. Additionally, the polymer can have combinations of two or more different diphenol monomer units with pendant phenyl ester groups, where the difference can be in the diphenol moiety, the phenyl ester moiety or the A moiety of the molecule. Additionally, the copolymers can have varying ratios of the A moiety when applicable, e.g., two different diacids or two different urethanes.

Examples of polymers of the invention having A as a diacid and mixed $R_1$ groups such that $R_1$ ranges overall from about 10% to about 50% bis-carboxypolyethylene glycol with the remaining $R_1$ being alkylene or $R_1$ ranges overall from about 10% to about 50% PEG-bis-succinate or PEG-bis-glutarate with the remaining $R_1$ being alkylene. Preferred alkylene groups for these polymers form the diacids succinic acid, glutaric acid, adipic acid or suberic acid.

When the polymer is a copolymer of one or more diphenol monomer units with a phenyl ester In accordance with various embodiments of the invention and other monomer units, then those other monomer units are any other compatible monomer unit that can polymerize with a diol and the A moiety of the diphenol moiety.

Hence those polymers of the invention which are copolymers containing a Monomer or a diphenol monomer unit of Formula II, can have other monomer units that are nearly the same as the Monomer or the diphenol monomer unit of Formula II, except that the phenyl ester moiety can be replaced by hydrogen (to form a free COOH group), by another ester class such as alkyl esters, alkylaryl esters, or esters with alkylene oxide chains or ether chains, by amides or by another compatible functional group. Alternatively, these slight variations can be combined with others where the other monomer units are similar to the Monomer or the diphenol monomer units of Formula II but now the have variability resides among the different substituents, i.e., the changes are in any of A, B, $R_1$-$R_{10}$, X, Y or the other variables of Formulas I and II. Finally, the other monomer units in the copolymer can be substantially different provided such moieties preserve the properties of the polymer and are capable of copolymerizing with the Monomer or the diphenol monomeric unit of Formula II.

Hence, in some embodiments, the other monomer unit is the same diphenol monomer wherein the phenyl ester moiety is replaced by, for example, a free carboxylic acid, an alkyl ester, an alkylaryl ester, an amide, an ether-containing ester, an ester with an alkylene oxide chain and the like. Examples of these and other diphenol monomers are described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as in U.S. Patent Application Publication Nos. 2002/0151668; 2003/0138488; 2003/0216307; 2004/0254334; 2005/0165203; and in PCT Publication Nos. WO99/52962; WO01/49249; WO01/49311; WO03/091337 and in U.S. Ser. No. 60/733,988, filed Nov. 3, 2005.

In accordance with various embodiments of the invention, the A moiety of the diphenol monomer in Formula II can be selected from a number of different groups to provide a variety of polymer classes.

When A is a carbonyl group, —C(O)—, then the polymers are polycarbonates. These polymers can be prepared by reaction with phosgene by methods known to those of skill in the art, including those described in U.S. Pat. No. 5,099,060. When A is —C(O)—$R_1$—C(O)—, then A, taken with the oxygens in the backbone, forms a diacid (i.e., these diacid-based ester groups present in the backbone, when hydrolyzed, form a diacid). For simplicity, A is sometimes referred to herein as a diacid (though this is clearly not strictly in keeping with the actual definition of A as used in the claims but is clear in context).

When A is a diacid, the polymers are polyarylates. For these polyarylates (as well as other polymers of the invention), $R_1$ is a divalent hydrocarbon group and can be linear or branched, substituted or unsubstituted. Such groups include alkyl, alkenyl, aryl, alkylaryl moieties having from 1 to 30 carbon atoms as well as larger alkylene oxide or arylene oxide moieties (based on the number of repeating units in those groups. As an example, when $R_1$ is an alkylene oxide, that group can be represented by the formula —$(R_2)_r$O$((CR_3R_4)_aO)_s(R_2)_r$- (with a, r, s, $R_2$, $R_3$ and $R_4$ as defined above which includes polyethylene glycol chains (PEG) such as —$CH_2O(CH_2CH_2O)_sCH_2$— or —$CH_2CH_2O(CH_2CH_2O)_sCH_2CH_2$— and polypropylene glycol chains such as —$CH_2CH_2CH_2O(CH_2CH_2CH_2O)_sCH_2CH_2CH_2$— and the like. Likewise, $R_1$ can be represented by the formula —$(R_2)_rCO_2((CR_3R_4)_aO)_sCO(R_2)_r$-. In a specific embodiment, this formula provides polymers which have PEG bis-succinate groups as A. for PEG bis-succinate, A is represented by the formula —C(O)$CH_2CH_2$C(O)O$(CH_2CH_2O)_s$C(O)$CH_2CH_2$C(O)—, where both $R_2$s are ethylene and $R_3$ and $R_4$ together form an ethylene group. If the formula is the same except that both $R_2$s are n-propylene, then the A moiety would be a PEG bis-glutarate.

In particular embodiments, the diacids formed by A include oxalic acid, malonic acid, succinic acid, glutaric acid, adipic acid, pimelic acid, suberic acid, azelaic acid, and sebacic acid, as well as diglycolic acid (where $R_1$ is —$CH_2OCH_2$—), dioxaoctanoic acid ($R_1$ is —$CH_2OCH_2CH_2OCH_2$—), alkylene oxide derivatives such as PEG, PEG bis-succinate and the like.

Methods of making polyarylates are known in the art. Such methods are found, for example, in U.S. Pat. Nos. 5,216,115; 5,317,077; 5,587,507; 5,670,602; 6,120,491; RE37,160E; and RE37,795E as well as in the literature, other patents and patent applications. Those of skill in the art can readily adapt these procedures to synthesize the polymers of the present invention.

When A is an imino group, —C(=NH)—, then the polymers are polyiminocarbonates. Polyiminocarbonates in general, and methods of their synthesis are described, e.g., in U.S. Pat. Nos. 4,980,449 and 5,099,060.

When A is —C(O)—N—$R_1$—NH—C(O)—, then the polymers of the invention are polyurethanes. Polyurethanes can be prepared as known in the art, for example, by a condensation reaction between a diol and a diisocyanate of the formula O=C=N—$R_1$—N=C=O to produce polyurethanes of the invention. The $R_1$ group is as defined hereinabove.

When A is a thionyl group, —C(S)—, then the polymers of the invention are polythiocarbonates. These polymers can be prepared, for example, by reaction with thiophosgene by methods known to those of skill in the art.

In accordance with various embodiments of the invention, the B moiety of the diphenol monomer in Formula II is a trivalent, linear or branched, substituted or unsubstituted alkyl, alkenyl, aryl or alkylaryl moiety having 1-20 carbon atoms. Any of the foregoing groups can contain one or more heteroatoms in the hydrocarbon chain or group such as O, N or S. Moreover, the substituents on the hydrocarbon chain or group can have heteroatoms as part of the substituents, such as provided by —$CF_3$, —$CH_2F$, —$NO_2$ and the like. In one embodiment of the invention B is

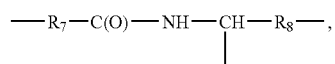

with $R_7$ and $R_8$ as defined herein and the CH bond is attached to the carboxyl of Formula II When $R_7$ and $R_8$ are both ethylene, then the B moiety taken with the diphenol rings, form the backbone portion of des-aminotyrosyltyrosine, which with a carboxyl group (—C(O)OH) attached to the CH group, is the free acid form of des-aminotyrosyltyrosine. In preferred embodiments, $R_7$ is independently a bond, a methylene or an ethylene group, and $R_8$ is independently a bond, a methylene or an ethylene group.

In accordance with various embodiments of the invention, each backbone aromatic ring of Formula II can have from zero to four $Z_1$ or $Z_2$ substituents. If the valence of a position on the aromatic ring, is not otherwise filled, then that position has a hydrogen atom. $Z_1$ or $Z_2$ are each independently selected from the group consisting of a halide, a lower alkyl, an alkoxy, a nitro, an alkylether, a protected hydroxyl, a protected amino and a protected carboxylic acid group.

When at least one of $Z_1$ or $Z_2$ is present and is bromine or iodine, then the polymer is radioopaque and has the uses described in U.S. Pat. No. 6,475,477. For example, use of radioopaque medical devices allows non-invasive techniques to monitor the presence and/or disappearance of the device, including the biodegradation and resorption of the device. Similarly, radioopaque microspheres formed from polymers of the invention may be useful as imaging agents or for drug delivery, and again can be monitored with non-invasive techniques such as x-ray, CAT scan, and the like.

Such polymers can be prepared from diphenol monomers units that have been halogenated prior to polymerization using standard halogenation reactions. While such reactions may tend to have preferred positions for the halogen atom on the aromatic ring (e.g., ortho), it is contemplated that the halogen atom can be at any available position.

In accordance with various embodiments of the invention, the pendant phenyl ring of Formula I and II has from zero to five R substituents on the phenyl ring and these substituents can be at any position. When no R group is present, then the ester of the polymer is an unsubstituted phenyl ester. When one R group is present, that R group is more readily added at the 2 or the 4 position (ortho or para). When two R groups are present, those R groups are generally at the 2 and 4 positions, but can also be at the 3 and 5 positions.

Accordingly, each R moiety when present on the pendant phenyl ring is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; —$(R_2)_rO((CR_3R_4)_aO_s$—$R_5$; —$O((CR_3R_4)_aO)_s$—$R_s$; —C(O)—$YR_6$; a protected hydroxyl group; a protected amino group or a protected carboxylic acid group.

When R is a substituted alkyl group, in addition to the other groups recited above in the definitions section, the substituents also be selected from —$CX_3$, —$CHX_2$, —$CH_2X$, —$R_2CX_3$, —$R_2CHX_2$ and —$R_2CH_2X$, wherein X is a halogen (F, Cl, I or Br) and $R_2$ is a lower alkylene or alkenylene group as defined herein. These groups thus include, trifluoromethyl, trifluoroethyl and the like. For example, if R is —$R_2CX_3$, $R_2$ is —$CH_2$— and X is F, then the R group is trifluoroethyl. For these substituents, preferred X is F or Cl and preferred $R_2$ is methylene or ethylene.

When R is an alkylaryl group, in addition to the other groups recited above in the definitions section, the alkylaryl group can be a trityl group.

When R is a heteroatom-containing alkyl group, in addition to the other groups recited above in the definitions section, that group can be trimethyl silane or N-hydroxysuccinimide.

When R is alkoxy, a preferred alkoxy group is —$OCH_3$.

R can also be represented by the formula —$(R_2)_bC(O)$—$YR_6$ where b is zero or one, Y is oxygen or nitrogen (i.e., O or N) and $R_2$ and $R_6$ are as defined herein. When Y is —O—, then the R group, taken as a whole, can be a free acid or an ester of benzoic acid, phenyl acetic acid, desaminotyrosine and the like. The preferred $R_6$ groups are hydrogen, methyl, ethyl, propyl, butyl (including t-butyl) and benzyl. By way of example, when b is zero, and $R_6$ is not hydrogen, the substituents are parabens, that is benzoic acid esters. In another example, when b is one and $R_2$ is methylene, the substituents are phenylacetic acid derivatives. When b is one and $R_2$ is ethylene, the substituents are desaminotyrosine derivatives, and if $R_2$ is ethenylene, the substituents are cinnamic acid derivatives.

The parabens are particularly useful phenyl ester groups, especially methyl paraben (MB), ethyl paraben (EB) and propyl paraben (PB). Another useful group is the ethyl ester of desaminotyrosine (DATE) as well as the corresponding free acid and methyl, propyl, t-butyl, and benzyl esters of desaminotyrosine.

When Y is —NH—, then the R group, taken as a whole, can be a free amine or an amide of benzoic acid, phenyl acetic acid, desaminotyrosine and the like. The preferred $R_6$ groups are hydrogen, methyl, ethyl, propyl, butyl (including t-butyl) and benzyl. By way of example, when b is zero, and $R_6$ is not hydrogen, the substituents are benzamides. In another example, when b is one and $R_2$ is methylene, the substituents are phenylacetamides. When b is one and $R_2$ is ethylene, the substituents are amides related to desaminotyrosine, and if $R_2$ is ethenylene, the substituents are cinnamides.

When R is an alkylene oxide, that group can be represented by the formula —$(R_2)_rO((CR_3R_4)_aO)_s(R_2)_r$, (with a, r, s, $R_2$, $R_3$ and $R_4$ as defined above) which includes polyethylene glycol chains (PEG) such as —$CH_2O(CH_2CH_2O)_sCH_2$— or —$CH_2CH_2O(CH_2CH_2O)_sCH_2CH_2$— and polypropylene glycol chains such as —$CH_2CH_2CH_2O(CH_2CH_2CH_2O)_sCH_2CH_2CH_2$— and the like. Likewise, $R_1$ can be represented by the formula —$(R_2)_rCO_2((CR_3R_4)_aO)_sCO(R_2)_r$. In a specific embodiment, this formula provides polymers which have PEG bis-succinate groups as A, namely A can be represented by the formula

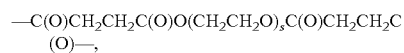

—C(O)$CH_2CH_2$C(O)O($CH_2CH_2$O)$_s$C(O)$CH_2CH_2$C(O)—, where both $R_2$s are ethylene and $R_3$ and $R_4$ together form an ethylene group. If the formula is the same except that both $R_2$s are n-propylene, then the A moiety would be a PEG bis-glutarate.

R can also be a protected hydroxyl, protected amine or protected carboxylic group. In addition to the uses of the invention, in some instances, polymers having such protected substituents can be used as intermediates to prepare other polymers of the invention. Protecting groups for OH, $NH_2$ and COOH groups are well known in the art and any are suitable for use in accordance with various embodiments of the invention, provided they are stable and compatible with the synthetic methods used to produce the polymers of the invention.

The $R_1$ is part of the A moiety of Formula II and has been described above. In particular, $R_1$ appears as part of the diacid moiety of A, i.e., as —C(O)—$R_1$—C(O)—, or as part of the urethane moiety, i.e., as —C(O)—NH—$R_1$—NH—C(O)—.

$R_2$, is independently a linear or branched lower alkylene or akylenylene group. In preferred embodiments, $R_2$ is methylene, ethylene or propylene.

When present in the group —$(R_2)_rO((CR_3R_4)_aO)_s(R_2)_r$, each $R_3$ and $R_4$ is independently a hydrogen or a linear or branched lower alkyl group. For example, if $R_3$ and $R_4$ are both hydrogen and a is 2, then that moiety is ethylene. Hence taken together and in combination with the value of a, $R_3$ and $R_4$ form a divalent alkyl groups, including but not limited to such as methylene, ethylene, propylene, butylene and the like.

In accordance with various embodiments of the invention, $R_5$ is independently linear or branched, substituted or unsubstituted, saturated or unsaturated alkyl. Preferred alkyl groups include methyl, ethyl, propyl, butyl (t-butyl, n-butyl, isobutyl) and the like.

$R_6$ has been described above and is part of the formula —$(R_2)_bC(O)$—$YR_6$. The preferred $R_6$ groups are hydrogen, methyl, ethyl, propyl, butyl (including t-butyl) and benzyl.

$R_7$ and $R_8$ have been described above and are each independently a bond, or linear or branched, substituted or unsubstituted alkyl, alkenyl or alkynyl having from 1 to 20 carbon atoms. When substituted, the substituent can be any of those described herein as well as —X, —$CX_3$, —$CHX_2$, —$CH_2X$, —$NHR_9$, or —$NHC(O)R_{10}$, provided that they are compatible with the chemistry needed to synthesize the polymer.

$R_9$, when present forms part of an amino group, is a linear or branched, substituted or unsubstituted, saturated or unsaturated alkyl, aryl or alkylaryl group or an amino protecting group.

$R_{10}$, when present forms part of an amide linkage and is a linear or branched alkyl, aryl or alkylaryl group.

The values of each a is independently one of the whole numbers 1, 2, 3 or 4. The value of each b is independently zero or one. When b is zero, the corresponding group is omitted and a single carbon bond is present. The value of each r is independently one of the whole numbers 1, 2, 3 or 4.

The value of each s is independently about 1 to about 5000 and determines the number of repeat units in the alkylene oxide chain. Hence, s can range from 1 to about 10, to about 15, to about 20, to about 30, to about 40, to about 50, to about 75, to about 100, to about 200, to about 300, to about 500, to about 1000, to about 1500, to about 2000, to about 2500, to about 3000, to about 4000 and to about 5000. Additionally, when the length of the alkylene oxide chain is related as a molecular weight, such as with PEG 200, PEG 400, PEG 600 and the like, then s need not be a whole number but can also be expressed as a fractional value, representative of the average number of alkylene oxide repeating units based on the cited (or a measured) molecular weight.

One group of preferred polymers of the invention are polyarylates in which the diphenol monomer unit of Formula II is selected such that A is —C(O)—$R_1$—C(O)—;

B is

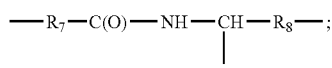

$R_1$ is, independently, a divalent, linear or branched, substituted or unsubstituted alkyl having from 1 to 30 carbon atoms; —$(R_2)_r$, $O((CR_3R_4)_aO)_s(R_2)_r$; or —$(R_2)_rCO_2((CR_3R_4)_aCO(R_2)_r$;

each $R_2$ is independently linear or branched, lower alkylene;

each $R_3$ and $R_4$ is independently hydrogen or linear lower alkyl; and $R_7$ and $R_8$ are each independently a bond, or linear or branched alkyl having from 1 to 20 carbon atoms.

Examples of polymers of the invention include, but are not limited to, poly(desaminotyrsosyl tyrosine methylparaben ester glutarate), also referred to as poly(DTMB glutarate);

poly(4-hydroxy-benzoic acid tyrosine methylparaben ester glutarate), also referred to as poly(BTMB glutarate);

poly(desaminotyrosyl tyrosine methylparaben ester succinate), also referred to as poly(DTMB succinate);

poly(4-hydroxy-benzoic acid tyrosine methylparaben ester succinate), also referred to as poly(BTMB succinate);

poly(desaminotyrsosyl tyrosine propylparaben ester succinate), also referred to as poly(DTPB succinate).

poly(4-hydroxy-benzoic acid tyrosine propylparaben ester succinate), also referred to as poly(BTPBsuccinate);

poly(desaminotyrsosyl tyrosine propylparaben ester glutarate), also referred to as poly(DTPBglutarate).

poly(desaminotyrosyl tyrosine methylparaben ester-co-10% desaminotyrsosyl tyrosine glutarate), also referred to as poly(DTMB-co-10DT glutarate);

poly(desaminotyrosyl tyrosine methylparaben ester-co-10% desaminotyrosyl tyrosine succinate), also referred to as poly(DTMB-co-10DT succinate);

poly((4-hydroxy-benzoic acid tyrosine methylparaben ester-co-15% (4-hydroxy-benzoic acid tyrosine glutarate), also referred to as poly(BTMB-co-1 OBT glutarate);

poly((4-hydroxy-benzoic acid tyrosine methylparaben ester-co-15% (4-hydroxy-benzoic acid tyrosine succinate), also referred to as poly(BTMB-co-10BT succinate);

poly(desaminotyrsosyl tyrosine DATE ester glutarate), also referred to as poly(DT(DATE)glutarate);

poly(desaminotyrsosyl tyrosine DATE ester glutarate), also referred to as poly(DT(DATE)glutarate); and poly(desaminotyrsosyl tyrosine DATE ester succinate), also referred to as poly(DT(DATE)succinate).

The structure of poly(DT(DATE)succinate) is shown below:

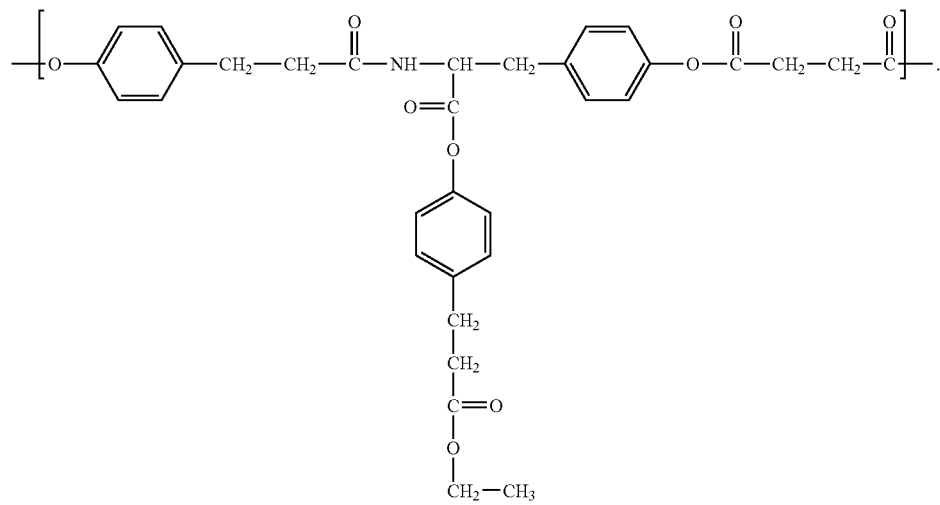

Synthesis:

The compounds of the invention can be synthesized by a variety of methods using techniques known in the polymer chemistry art. In one method, the first step is preparation of the monomer unit with the desired pendant phenyl ester followed by polymerization of the monomer unit to produce a polymer of the invention.

For example, if the monomer unit used in the polymerization step is a diol (e.g., to form a polyester, polyesteramide, polyarylate or other such polymer), the hydroxyl groups are protected while the phenyl ester derivative is prepared. To do this one can begin with the diol monomer with a pendant carboxyl group derivatized with a relatively stable ester group (e.g., an alkyl group such as methyl or ethyl). The diols are then protected with a protecting group under conditions in which ester is stable. The ester is converted to the free acid with hydrolyzing the diol protecting groups. The free acid can be reacted with a hydroxyaryl compound to produce the monomer unit bearing a phenyl ester. The diol protecting groups are removed under conditions that do not affect the stability of the phenylester, and the resulting monomers can be polymerized. A similar strategy can be used for other polymers with free amines or other reactive polymerization groups.

By way of an example, desaminotyrosyl tyrosine methyl ester (DTM) is reacted with benzylbromide to produce bis-benzyl-DTM which is converted to the free acid form, bis-benzyl-DT. That free acid is reacted with methylparaben to produce bis-benzyl-DTMB. After debenzylation, one obtains DTMB, which can then be polymerized by methods know in the art.

In an alternative method, polymers containing pendant phenyl esters can be prepared in a three step process. In the first step, a precursor polymer containing a protected pendant group is prepared. In the next step, the pendant protecting group is removed without degrading the polymer backbone. In the final step, the phenyl ester is attached to the polymer backbone, via the unprotected functionality. In general the polymer with pendant free carboxylic acid groups is synthesized in a two step process by polymerizing monomer units having a protecting group on the carboxylic acid, e.g., an alkyl ester, a benzyl ester, or any other protecting group such as those used in peptide chemistry, followed by removal of the protecting group without backbone degradation to yield the free acid-containing precursor polymer. That polymer is then derivatized with a phenol compound (i.e., the desired hydroxyaryl compound) to produce a polymer of the invention.

For example, a tyrosine-derived polyarylate with a phenyl ester side chain can be prepared by reacting equimolar amounts of the desired diphenol monomer that has a benzyl ester side chain (e.g., desaminotyrosyl tyrosine benzyl ester) and the desired diacid (e.g., succinic acid) in an organic solvent (e.g., a chlorinated solvent such as methylene chloride) in the presence of the catalyst dimethyaminopyridinium-para-toluenesulfonate (DPTS). Once the compounds are dispersed in the solvent, a coupling agent, such as diisopropylcarbodiimide (DIPC), is added in molar excess and the reaction is allowed to proceed until the mixture becomes viscous, typically at room temperature. The benzyl protected polymer can be isolated by repeated precipitation from nonsolvent and dried.

One method to remove the benzyl protecting group, is to dissolve the polymer in organic solvent and bubble nitrogen through the solution for a time sufficient to remove all oxygen. A palladium catalyst such as Pd/BaSO$_4$ is added after stopping the nitrogen. Hydrogen gas is then passed through the reaction mixture which is stirred overnight or until there is no benzyl remaining on the polymer. The completion of the hydrogenation reaction can be monitored by techniques known to those of skill in the art such as NMR, HPLC or gas phase chromatography. Other methods of hydrolysis, such as differential acid hydolysis, can be used to remove the protecting group on the pendant carboxyl group provided that the backbone of the polymer remains intact, i.e., does not degrade or does not significantly degrade, under the reaction conditions. The free carboxylic acid-containing polymer can be isolated by known techniques, preferably, e.g., by precipitation, with drying to constant weight.

The free acid polymer is dissolved in organic solvent, and a slight molar excess of the desired phenolic compound is added if every position is to be derivatized to a phenyl ester. To produce a polymer with a particular percentage of free acid, the amount of the phenolic compound is reduced by the desired percent of free acid. For example to prepare a polymer with 80% methyl paraben and 20% free acid (i.e., DTMB-20-DT glutarate), a slight excess over 0.8 mole equivalents of 4-hydroxy methyl paraben is used in the reaction. A slight molar excess can be determined empirically to obtain the desired percentage substitution in the final polymer preparation; typically about 5-10% molar excess is sufficient. After mixing the reactants, the mixture is cooled, a suitable coupling agent such as DIPC is added, and stirring continued until the reaction is complete. The final polymer is isolated, e.g., by aqueous precipitation, filtered and dried to constant weight.

Polymers of the invention can be purified by methods known to those of skill in the art, such as by precipitation, by chromatography and the like.

Monomers:

The present invention is also directed to diphenol monomers having pendant phenyl ester groups. The monomers of the invention are useful as intermediates to prepare the polymers of the present invention and are represented by Formula III or IV

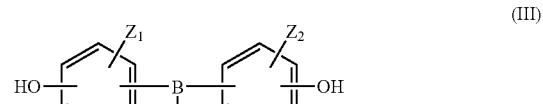

(III)

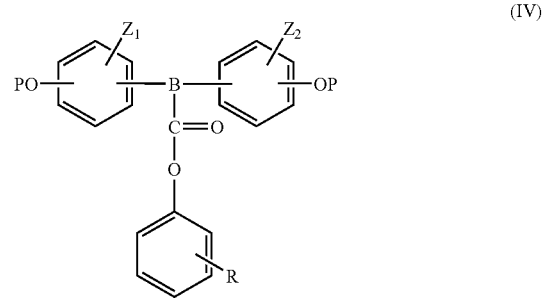

(IV)

wherein

B is a trivalent, linear or branched, substituted or unsubstituted alkyl, alkenyl, aryl or alkylaryl moiety having 1-20 carbon atoms, or is

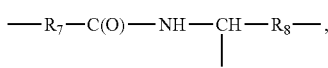

each backbone aromatic ring has from zero to four $Z_1$ or $Z_2$ substituents, each of which is independently selected from the group consisting of halide, lower alkyl, alkoxy, nitro, alkylether, a protected hydroxyl group, a protected amino group and a protected carboxylic acid group;

the pendant phenyl ring has from zero to five R substituents at any position on the phenyl ring, and each R is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; $-(R_2)_rC((CR_3R_4)_aO)_s-R_5$; $-O((CR_3R_4)_aO)_s-R_5$; $-C(O)-R_5$; $-(R_2)_bC(O)-YR_6$; a protected hydroxyl group; a protected amino group or a protected carboxylic acid group;

each $R_2$ is independently linear or branched, lower alkylene or lower alkenylene;

each $R_3$ and $R_4$ is independently hydrogen, or linear or branched lower alkyl;

$R_5$ is independently linear or branched, substituted or unsubstituted, saturated or unsaturated alkyl;

$R_6$ is hydrogen; saturated or unsaturated alkyl, aryl or alkylaryl having from 1 to 20 carbon atoms; or $-(R_2)_rO((CR_3R_4)_aO)_S-R_5$;

$R_7$ is independently a bond, or linear or branched, substituted or unsubstituted alkyl, alkenyl or alkynyl having from 1 to 20 carbon atoms, and when substituted, the substituent can be, but is not limited to, $-X$, $-CX_3$, $-CHX_2$, $-CH_2X$, $-NHR_9$, or $-NHC(O)R_{10}$;

$R_8$ is independently a bond or linear or branched, substituted or unsubstituted alkyl, alkenyl or alkynyl having from 1 to 20 carbon atoms, and when substituted, the substituent can be, but is not limited to, $-X$, $-CX_3$, $-CHX_2$, $-CH_2X$, $-NHR_9$, or $-NHC(O)R_{10}$;

$R_9$ is a linear or branched, substituted or unsubstituted, saturated or unsaturated alkyl, aryl or alkylaryl group or an amino protecting group;

$R_{10}$ is a linear or branched alkyl, aryl or alkylaryl group;

P is an $-OH$ protecting group;

X is a halogen;

Y is $-O-$ or $-NH-$;

each a is independently 1 to 4;

each b is independently zero or one;

each r is independently 1 to 4; and each s is independently 1 to 5000.

The embodiments of, and preferred embodiments for, B, $R_2$, $R_3$, $R_4$, $R_5$, $R_6$, $R_7$, $R_8$, $R_9$, $R_{10}$, X and Y are as described above in the polymer section. The values, including the preferred values, for a, b, r and s are as described above in the polymer section.

As used herein, P is a protecting group for the hydroxyls on the diphenol (backbone) rings of the monomer. Such protecting groups are stable under the chemical conditions needed to remove an alkyl ester (or other carboxylic acid protecting group) from the position occupied by the phenyl ester (and thereby make the free acid equivalent of these molecules). Such protecting groups are also stable under the chemical conditions needed to react a hydroxyaryl compound with the protected monomer and thereby produce a protected monomer bearing a phenyl ester moiety as shown. Finally the protecting groups can be removed from the monomer under conditions which do not cause hydrolysis of the phenyl ester. Benzyl is a suitable protecting group, but many others are known in the art, see, e.g., T. W. Greene and P. G. M. Wuts, *Protecting Groups in Organic Synthesis,* 3rd ed., John Wiley & Sons, Inc., New York, 1999.

Uses

The polymers of the invention are biocompatible, biodegradable polymers comprising monomer units with pendant phenyl ester (PE) groups, i.e., PE side chains relative to the polymer backbone. The PE groups are good leaving groups under physiological conditions and thus provide a means to generate free pendant carboxylic moieties in vivo which leads to rapid breakdown and resorption of the polymer. With the polymer being driven to breakdown more quickly into more water-soluble constituents, the result is faster resorption in use, especially when compared to a similar polymer with alkyl esters replacing the equivalent amount of phenyl esters.

For example, desaminotyrosyltyrosine ethyl ester succinate resorbs in about 1 year but when the ethyl ester is replaced by a paraben ester, the resorption time is less than 3 months.

Breakdown of the polymer can be measured in a variety of ways. The in vivo degradation process can be mimicked in vitro in several ways. By aging a polymer-coated device (or a composition or device formed primarily from a polymer of the invention) at 37° C. in phosphate buffered saline at pH 7.4, the hydrolytic processes may be reproduced. If oxidative mechanisms are relevant then the same solution may be supplemented with oxidants such as hydrogen peroxide or superoxide salts. Additionally, if enzymatic degradation processes are important, representative enzymes can be added to the solution. It is to be understood that while such in vitro tests can mimic the chemical processes operant in vivo, they predict kinetics and rates inaccurately. Further, as needed, in vivo animal models can be used to correlate in vivo and in vitro degradation behavior.

In addition to measuring polymer degradation and resorption, those of skill in the art can monitor drug release using the same techniques as well as others. For example, antibiotic activity can be measured by zone of inhibition assays, pain relief can be measured in animal models for pain and more.

The polymers of the invention are relatively more hydrophobic before breakdown, and this provides a useful ability to solublize drugs or act as a reservoir for a wide variety of drugs, in addition to being able to manipulate the drug release profile. Since a variety of substituents can be used on the polymers, such as PEGs, hydrophobic groups and many others, the polymer can be readily manipulated for purposes of both drug formulations and for controlled or sustained release. Those of skill in the art can thus manipulate the chemical constituents of the polymers to achieve particular release profiles for compositions, for coated devices or for resorbable devices (whether fully or partially resorbable)—in the context of the faster resorption times provided by the polymers of the invention.

Hence, the polymers of the invention have a myriad of biological uses when a biocompatible, biodegradable polymer is needed, for coating medical devices, to form fully or partially resorbable medical devices, to deliver drugs in specific manners (either in conjunction with such device or as part of a pharmaceutical composition comprising the polymer, a drug and other agents). It should be understood that the polymers are useful without the presence of drugs. For example, a polymer coating on a surgical mesh can increase mesh stiffness, and thereby allow easier handling at the time of implantation yet still provide a mesh that softens over time and is comfortable for the patient. Moreover, a polymer-coated, flat mesh can be formed into a three dimensional shape, and this can be useful in surgical repairs. Fully resorbable devices can be used as sutures intended to impart strength for a period before dissolving, as temporary wound closures, such as a femoral plug, and the like.

Further uses for the polymers of the invention are described in detail, for example, in U.S. Ser. No. 11/672,929, filed Feb. 8, 2007 which describes coated surgical meshes for a variety of applications; in U.S. Ser. No. 60/864,597, filed Nov. 6, 2006 which describes fully and partially resorbable coverings, pouchs, bags and coated meshes for cardiac rhythm management devices, neurostimulators as well as for other implantable medical devices; and in U.S. Ser. No. 60/908, 960, filed Mar. 29, 2007 and in PCT/US08/58652, filed Mar. 28, 2008, for resorbable coverings for breast implants.

The compositions of the present invention can be used to faun medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and resorption rate; and (iv) that can be combined with drugs that are not only bioactive and/or biobeneficial but also control a physical property and/or a mechanical property of a medical article or coating formed from the polymer.

Blends:

An additional way to manipulate drug release and resorption characteristics is to blend polymers. Accordingly, the present invention provides blends of the polymers of the invention with other biocompatible polymers, preferably other biodegradable polymers. These other polymers include, but are not limited to, polylactic acid, polyglycolic acid and copolymers and mixtures thereof such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); poly(oxa)esters, polyethylene oxide (PEO), polydioxanone (PDS), polypropylene fumarate, poly (ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), other tyrosine-derived polyarylates, other tyrosine-derived polycarbonates, other tyrosine-derived polyiminocarbonates, other tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

Using blends provides many advantages, including the ability to make partially resorbable devices and fully resorbable devices that have varied resorption times for parts or all of the device. For example, a partially resorbable device may increase porosity over time and thus permit tissue in growth. Those of skill in the art can readily pick combinations of polymers to blend and determine the amounts of each polymer need in the blend to produce a particular product or achieve a particular result.

Drugs:

Any one or more drug, biological agent, or active ingredient that is compatible with the polymers, monomers and blends of the invention can be incorporated in, formed into or used in conjunction or combination with a pharmaceutical composition or a medical device coated or formed from the polymers, monomers or blends of the invention. Doses for such drugs and agents are known in the art. Hence, those of skill in the art can determine the amount of drug or agent desired for delivery, and calculates the amount needed for the desired application, based on size of the device, coating thickness, effective doses and the like.

In accordance with various embodiments of the invention, drugs and biologically-active agents include, but are not limited to, anesthetics, antimicrobials (which include antibiotics, antifungal agents and antibacterial agents), anti-inflammatory agents, fibrosis-inhibiting agents, anti-scarring agents, cell growth inhibitors, growth factors and the like.

As used herein, "drugs" is used to include all types of therapeutic agents, whether small molecules or large molecules such as proteins, nucleic acids and the like. The drugs of the invention can be used alone or in combination.

Examples of non-steroidal anti-inflammatory agents include, but are not limited to, acetominophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine.

Examples of anesthetics include, but are not limited to, lidocaine, bupivacaine, mepivacaine and xylocaine. Local anesthetics have weak antibacterial properties and can play a dual role in the prevention of acute pain and infection.

Examples of antimicrobial drugs include, but are not limited to, aminoglycosides such as amikacin, gentamicin, kanamycin, neomycin, streptomycin, and tobramycin;

antibiotics such as bacitracin, clindamycin, daptomycin, lincomycin, linezolid, metronid, polymyxin, rifaximin, vancomycin;

cephalosporins such as cephazolin;

macrolide antibiotics such as erythromycin, azithromycin and the like;

β-lactam antibiotics such as penicillins;

quinolones such as ciprofloxacin;

sulfonamides such as sulfadiazine;

tetracyclines such as minocycline and tetracycline; and other antibiotics such as rifampin, triclosan, chlorhexidine, sirolimus and everolimus.

Other drugs that can be used include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, nicotinic acid, chemodeoxycholic acid, chlorambucil and anti-neoplastic agents such as paclitaxel, sirolimus, 5-flurouracil and the like. Examples of useful proteins include cell growth inhibitors such as epidermal growth factor antagonists.

Preferred antimicrobial agents of the invention include rifampin, minocycline, gentamicin, vancomycin, triclosan, sirolimus and everolimus, alone or in combination. Rifampin and minocyline are a preferred combination of anti-microbial agents.

Leukotriene inhibitors/antagonists are anti-inflammatory agents and include, but are not limited to, leukotriene receptor antagonists such as acitazanolast, iralukast, montelukast, pranlukast, verlukast, zafirlukast, and zileuton.

Pharmaceutical Formulations:

The polymers and blends of the invention can be formulated as pharmaceutical compositions comprising one or more of those molecules, one or more drugs (as active ingredient), and a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are well known. In addition to the pharmacologically active agent, the compositions can contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds, as appropriate in injection suspensions may be administered. Suitable lipophilic solvents or vehicles include fatty oils, for example, sesame oil or synthetic fatty acid esters, for example, ethyl oleate or triglycerides. Aqueous injection suspensions can contain substances which increase the viscosity of the suspension include, for example, sodium carboxymethyl cellulose, sorbitol, and dextran. Optionally, the suspension can also contain stabilizers. Liposomes can also be used to encapsulate the agent for delivery into cells.

The pharmaceutical formulation for systemic administration according to the invention can be formulated for enteral, parenteral or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The polymers and blends of the invention can also be incorporated into pharmaceutical compositions which allow for the sustained delivery of those compounds to a mammal for a period of several days, to at least several weeks, to a month or more. Such formulations are described in U.S. Pat. Nos. 5,968,895 and 6,180,608 B1.

For topical administration, any common topical formation such as a solution, suspension, gel, ointment or salve and the like can be employed. Preparation of such topical formulations are well described in the art of pharmaceutical formulations as exemplified, for example, by Remington's Pharmaceutical Sciences. For topical application, the polymers and blends of the invention can also be administered as a powder or spray, particularly in aerosol form. The active ingredient can be administered in pharmaceutical compositions adapted for systemic administration. As is known, if a drug is to be administered systemically, it can be confected as a powder, pill, tablet or the like or as a syrup or elixir for oral administration. For intravenous, intraperitoneal or intra-lesional administration, the active ingredient can be prepared as a solution or suspension capable of being administered by injection. In certain cases, it may be useful to formulate the active ingredient in suppository form or as an extended release formulation for deposit under the skin or intramuscular injection. In a one embodiment, the polymers and blends of the invention may facilitate inhalation therapy. For inhalation therapy, the polymers or blends together, with the active ingredient, can be in a solution useful for administration by metered dose inhalers or in a form suitable for a dry powder inhaler.

Medical Devices:

The polymers and blends of the invention can be used to coat or form implantable prostheses used to reconstruct, reinforce, bridge, replace, repair, support, stabilize, position or strengthen any soft tissue defect. For example, soft tissue defects that can be treated in accordance with various embodiments of the instant invention including hernias, such as but not limited to inguinal, femoral, umbilical, abdominal, incisional, intramuscular, diphragmatic, abdomino-throacic and thoracic hernias. The prostetheses can also be used for structural reinforcement for muscle flaps, to provide vascular integrity, for ligament repair/replacement and for organ support/positioning/repositioning such as done with a bladder sling, a breast lift, or an organ bag/wrap. The prostetheses can be used in recontruction procedures involving soft tissue such as an orthopaedic graft support/stabilization, as supports for reconstructive surgical grafts and as supports for bone fractures.

The prostheses are generally meshes, membranes or patches, and include woven or non-woven meshes and the like.

Additionally, the polymers and blends of the invention can be used to coat or to form wound closure adjuncts, such as staples, sutures, tacks, rings, screws, and the like.

The polymers and blends of the invention can also be used to coat meshes which are formed into or to form pouches, coverings, pockets and the like for implantable medical devices. Such implantable medical devices include, but are not limited to cardiac rhythm management devices such as a pacemaker, a defibrillator, a pulse generator as well as other implantable devices such as implantable access systems, neurostimulators, spinal cord stimulators, breast implants or any other implantable medical device. The coverings, pouches, pockets and the like hence can serve to secure those devices in position, provide pain relief, inhibit scarring or fibrosis, inhibit or prevent bacterial growth or infection, and deliver other drugs to the site of implantation.

The polymers and blends of the invention can also be used in conjunction with any implantable or insertable medical devices which has a temporary, or some time-limited therapeutic need as well as those with permanent function (such as joint replacements). For example, such polymers can be used to form fully resorbable vascular stents, which after a sufficient period of healing become completely resorbed while leaving a, patent blood vessel. Fully resporbable stents may be used in conjunction with one or more drugs.

More detail and other examples of medical devices to which the present polymers and blends are useful include, but are not limited to, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, femoral plugs, patches, pacemakers and pacemaker leads, heart valves, vascular valves, biopsy devices, patches for delivery of therapeutic agent to intact skin and broken skin (including wounds); tissue engineering scaffolds for cartilage, bone, skin and other in vivo tissue regeneration; sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and various coated substrates that are implanted or inserted into the body.

Use of the polymers and blends with any of the medical devices described herein can include can be used with one or more drugs.

Accordingly, the present invention provides methods of treating a disorder or condition in a patient comprising implanting a medical device or a medical device assembly comprising a polymer or blend of the invention, e.g., as a coating, in conjuction with a covering or as the complete or partial device, by implanting the device in a patient, and particularly for disorders and conditions such as a cardiovascular disorder, a neurological disorder, a hernia or hernia-related disorder, an ophthalmic condition, or anatomical repair, reconstruction, replacement or augmentation.

In some embodiments, the method is used to implant a stent to treat atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

In other embodiments, the method is used to implant a surgical mesh to reconstruct, reinforce, bridge, replace, repair, support, stabilize, position or strengthen any soft tissue defect, including a hernia.

In yet other embodiments, the method is used to implant a medical device assembly such as a CRM in a covering or pouch, a neurostimulator in a pouch or covering, or a breast implant in a pouch or covering.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety for all purposes.

Example 1

Synthesis of Poly(desaminotyrsosoyl tyrosine methylparaben ester glutarate)

A. Preparation of poly(DTBn-glutarate)

DTBn (0.5 mol, 209.66 g), glutaric acid (0.5 mol, 66.06 g), DPTS (0.2 mol, 58.84 g) were placed in a 3 L flask equipped with an overhead stirrer and condenser. Methylene chloride (1.2 L) was added to the flask and the contents stirred until all the solids were dispersed. DIPC (1.5 mol, 189.3 g, 234.2 mL) was added and stirring continued for 20-22 h by which time reaction mixture was viscous. The polymer was isolated by repeated precipitations from methylene chloride and isopropanol (IPA). The solid polymer was transferred to a polypropylene tray and left to dry in the hood overnight, transferred to a vacuum oven at 50° C. and dried to constant weight. The yield of poly(DTBn-glutarate) was 203 g (76%). The polymer had a molecular weight of 100 kDa and a $T_g$ of 66° C.

B. Removal of Pendant Benzyl Esters to Produce poly(DT-glutarate)

A 5% solution of poly(DTBn-glutarate) was prepared by dissolving 200 g of the polymer in 4 L dimethylformamide (DMF). Nitrogen was bubbled through the clear solution for about 30 minutes. While stirring, 54 g of catalyst (5% Pd on $BaSO_4$; 27% w/w with respect to the benzyl precursor polymer) was added all at once. Hydrogen gas was bubbled through the solution and stirring continued overnight. The reaction mixture was filtered on a Celite bed (celite is a diatomaceous filter aid) and the de-benzylated polymer was precipitated in cold water. The wet polymer cake was dried to constant weight under vacuum. The yield of poly(DT-glutarate) was 142 g (71%). The polymer had a molecular weight of 95 kDa and a $T_g$ of 111° C.

C. Addition of Methyl Paraben to Produce poly(DTMB-glutarate):

Poly(DT-glutarate) (0.0564 mol, 25 g) was dissolved in 150 mL DMF in a 250 mL round-bottom flask. While stirring, p-hydroxy methyl benzoate (0.225 mol, 34.3 g) was added (Molar ratios as low as a 10% excess are also effective). The flask was then cooled in an ice water bath. Successively, dimethylaminopyridine (DMAP) (0.55 g, 0.0045 mol) and then DIPC (0.062 mol, 7.83 g, 9.7 mL) were added to the flask. After 15 min, the flask was removed from the ice water bath and the reaction allowed to proceed overnight. The reaction mixture was slightly viscous and was treated with 4 mL of glacial acetic acid. The urea formed was filtered through a sintered funnel to obtain the clear filtrate. With stirring, the polymer-containing filtrate was added to 550 mL of solvent 9:1 IPA:methanol. The precipitated polymer was washed with twice with 100 mL IPA, redissolved in 500 mL of DMF and poured into 3 L of 20% aqueous NaCl to precipitate the poly(DTMB-glutarate). The precipitated polymer was collected on a sintered funnel under vacuum, transferred to a glass dish, dried overnight in a hood, and then dried in a vacuum oven to constant weight. The yield of poly(DTMB-glutarate) was 17 g (52%). The polymer had molecular weight of 60 kDa and a $T_g$ of 71° C.

Example 2

Synthesis of Poly(desaminotyrososyl tyrosine propylparaben ester glutarate)

The polymer poly(desaminotyrsosyl tyrosine propylparaben ester glutarate), i.e., poly(DTPB glutarate), was synthesized as described in Example 1 except that in step C, phydroxy propyl benzoate (0.225 mol, 40.5 g) was added to the solution of poly(DT-glutarate) in DMF. The remainder of the polymer work up remained the same and yielded poly(DTP-Bglutarate) 21 g (61%). The polymer had molecular weight of 70 kDa and a $T_g$ of 66° C.

Example 3

Sythesis of Poly(desaminotyrosyl tyrosine methylparaben ester succinate)

The polymer poly(desaminotyrsosyl tyrosine methylparaben ester succinate), i.e., poly(DTMB succinate), was synthesized as described in Example 1 except that in step C, glutaric acid was replaced with succinic acid. The remainder of the polymer work up and synthesis generally remained the same and yielded poly(DTMB-succinate) 18 g (54%). The polymer had a molecular weight of 40 kDa and a $T_g$ of 76° C.

Example 4

Synthesis of Poly(desaminotyrosyl tyrosine Methylparaben ester-co-10% desaminotyrosyl tyrosine succinate)

To prepare a polymer with free acid monomer, the synthesis of Example 1 is followed, except that in step A, succinic acid is substituted for glutaric acid and in step C, 0.9 equivalents of methylparaben is added to poly(DT) to yield poly(DTMB-10-DT succinate).

Example 5

Synthesis of Poly(desaminotyrosyl tyrosine DATE ester glutarate)

The polymer poly(desaminotyrsosyl tyrosine DATE ester glutarate), i.e., poly(DT(DATE) glutarate), was prepared from poly(DT glutarate) obtained as described in Example 1, steps A and B. The ethyl ester of desaminotyrosyl tyrosine was prepared as described in step A below and reacted with poly(DT glutarate) as described in step B below to produce the final product, poly(DT(DATE) glutarate).

A. DATE Preparation

To prepare DATE, a solution of 3-[4-hydroxyphenyl]propionic acid (24.2 g, 0.146 mol) in 300 mL of 200 proof ethanol containing 47 mL 4 M HCl/dioxane was mixed at reflux for 4 h. After distilling away much of the solvent, the residue was rotary evaporated at 65° C. under vacuum to render a yellow liquid (30 g). This liquid residue was dissolved in 75 mL toluene and extracted twice with 3% $NaHCO_3$/14% NaCl (75 mL) followed once by 75 mL 20% NaCl. The toluene solution was dried over anhydrous magnesium sulfate and rotary evaporated to leave a further liquid residue which was further co-evaporated with 50 mL portions of toluene. After the final evaporation, the residue was dried in a vacuum oven to yield 25 g of a moderately viscous yellow liquid with virtually no odor of toluene. TLC (silica gel with a 9:1 methylene chloride:methanol solvent system) showed a single spot at an $R_f$ of 0.50 when visualized by UV and iodine. NMR ($D_6$MSO): 1.3 ppm (t, 3H), 2.5-2.9 ppm ($a^2b^2$, 4H), 4.1 ppm (q, 3H), 6.7-7.1 ppm (ab, 4H), 9.4 ppm (s, 1H).

B. DATE Addition to poly(DT glutarate)

The DATE prepared in step A (0.125 mol, 24.3 g) and poly(DT glutarate) (0.034 mol, 14.5 g) were dissolved in 125 mL DMF and the solution was cooled in an ice-water bath. DIPC (0.042 mol, 6.6 mL) was added to the solution, after stirring for 5 min, DMAP (0.0028 mol, 0.34 g) was added and stirring continued overnight in the ice bath (which was allowed to come to room temperature during that time). The reaction mixture was added rapidly dropwise to 1200 mL (9:1 IPA:methanol, resulting in an elastomeric precipitate. The solvents were decanted and the solid washed twice with 1200 mL IPA containing 0.5 mL of glacial acetic acid. The washed solid was dissolved in 150 mL DMF containing 1 mL glacial acetic acid, filtered and re-precipitated by rapid dropwise addition to 1800 mL distilled water. This precipitate was resuspended twice in 1 L of cold distilled water, filtered over a polypropylene membrane and washed several times with distilled water before drying at 45° C. for several days in a vacuum oven. The poly(DT(DATE) glutarate) had a molecular weight of 82 kDa as determined by gel permeation chromatography (DMF/0.1% TFA, 0.8 mL/m, PEG standards) and a $T_g$ of 43.03° C. NMR: ($D_6$MSO): 1.6 ppm (t, 3H), 4.1 ppm (q, 2H).

Example 6

Alternate Synthesis Route for Poly(DTMB glutarate) and Poly (DTMB succinate)

A. Monomer Preparation

A mixture of DTM (18.8 g, 0.0548 mol), potassium carbonate (16.6 g, 0.1205 mol) and benzyl bromide (13.7 mL, 0.1150 mol) were refluxed in 100 mL of acetone for 16 h. The reaction mixture was added to 260 mL of dichloromethane, stirred and filtered through a fine porosity sintered funnel. The clarified filtrate was concentrated on a rotary evaporator to yield a slush. The slush was diluted with 800 mL hexane and stirred to produce a smooth suspension. The solid was filtered and vacuum dried at 40° C. to yield 25 g of the bis-benzyl derivative which showed a single $R_f$ spot on silica gel TLC (9:1 methylene chloride:methanol) at 0.77 when visualized by UV and iodine. NMR: 3.7 ppm (s, 1H), 4.4 ppm (m, 1H), 5.1 ppm (s, 4H), 6.8-7.4 ppm (m, 18H), 8.4 ppm (d, 1H).

A mixture of bis-benzyl DTM (25.3 g) and NaOH (61.4 g) was stirred in 600 mL distilled water at 95-100° C. for 20 min. The mixture was cooled in a ice bath, the pH was adjusted to 2.5 by adding 8 M HCl, and filtered over a sintered glass funnel. The white crystalline solid was dried under vacuum at 40° C. for 2 days, 23.7 g. Silica gel TLC (9:1 methylene chloride:methanol with 1% acetic acid) showed a single spot at $R_f$ 0.41 when visualized by uv and iodine. mp: 201.7° C. NMR: 4.4 ppm (m, 1H), 5.1 ppm (s, 4H), 6.87.4 ppm (m, 18H), 8.2 ppm (d, 1H), 12.7 ppm (s, 1H).

A mixture of bis-benzyl-DT (26.6 g, 0.0522 mol), methyl paraben (7 g, 0.0493 mol) and DPTS (7.8 g, 0.0265 mol) was stirred in 117 mL of N-methylpyrrolidinone for 15 min at room temperature, and the temperature lowered to 2-5° C. in an ice-water bath. DIPC (8.8 mL, 0.0562 mol) was added to the cooled solution and the mixture stirred overnight in the ice-bath (without refreshment). The mixture was kept in a freezer for 3-4 h before filtering to remove the diisopropylurea solid. The clarified filtrate was added to 3200 mL cold, distilled water with stirring continued overnight or until coagulation of the milky solid was complete. The white solid product was isolated by filtration and dried under vacuum at 40° C. The dried solid (32 g) was recrystallized from a solution of 470 mL ethanol (200 proof) with 90 mL of glacial acetic acid and vacuum dried at 30° C. to yield 21 g white crystalline product, bis-benzyl-DTMB. Silica gel TLC (9:1 methylene chloride:methanol with 1% acetic acid) showed a single spot at an $R_f$ of 0.55 when visualized by uv and iodine. Methylparaben was not detected. NMR: 2.4 ppm (m, 2H), 2.7 ppm (m, 2H), 3.1 ppm ($a^2b^2$, 2H), 3.9 ppm (s, 3H), 4.6 ppm (q, 1H), 5.1 ppm (s 2H), 5.2 ppm (s, 2H), 6.8-7.9 ppm (m, 22H), 8.6 ppm (d, 1H).

A solution of bis-benzyl-DTMB (21.6 g) in 162 mL DMF was hydrogenated over 7.9 g of Pd/C (10%) at atmospheric pressure for 10-12 h. The mixture was diluted with 400-500 mL of ethyl acetate and catalyst was removed by filtration through filter paper followed by two extractions with 600 mL 20% NaCl, two extractions with 500 mL 3% $NaHCO_3$/14% NaCl and two extractions with 300 mL 20% NaCl. The clarified solution was dried over anhydrous magnesium sulfate and concentrated to a stiff gum in a rotary evaporator. Repetitively mixing the gum with methylene chloride and rotary evaporating to produce the gum, followed by submersion of the gum under hexane for several days led to a white crystalline solid. After filtration and vacuum drying, the yield was 12.2 g DTMB having a melting point of 132° C. Silica gel TLC (9:1 methylene chloride: methanol with 1% acetic acid) showed a major spot at an $R_f$ of 0.35 when visualized by UV and iodine. NMR: 2.4 ppm (m, 2H), 2.6 ppm (m, 2H), 2.8 ppm (m, 2H), 3.7 ppm (s, 3H), 4.5 ppm (m, 1H), 6.6-8.0 ppm (m, 12H), 8.5 ppm (d, 2H), 9.1 ppm (s, 1H), 9.3 ppm (s, 1H); elemental: % C, 67.71, % H, 5.16, % N, 3.03: theory: % C, 67.38, % H, 5.44, % N, 3.02.

B. Polymerization

To form poly(DTMB glutarate) or poly(DTMB succinate), the DTMB monomer is polymerized with glutaric acid or succinic acid, respectively, according to the method described in Example 1, step A.

Example 7

In Vivo Mass Loss Studies

To analyze the mass loss and degradation profile, polypropylene mesh which had been laser cut into small pieces was dip coated with the indicated polymer to provide an average of 3-5 mg polymer on an average of 5 mg of mesh. The coated meshes were dried at room temperature for 24 h and then dried in a vacuum oven for 3 days. In some instances, the polymers were spray coated onto large meshes, cut to the desired size and implanted. After weighing, the coated meshes were sealed into PMMA chambers (size: d=1 cm and h=0.5 cm) with Nylaflo Nylon membrane filters.

The sealed chambers were implanted subcutaneously onto the back of the rabbits placing five chambers with samples and one control chamber with plain mesh on each side of the back of each rabbit.

Chambers were surgically removed at the indicated time points and the meshes were analyzed for polymer mass loss and molecular weight changes. The polymer on the mesh is dissolved by soaking in DMF containing 0.1% TFA. The solution is filtered through 0.45μ Teflon® syringe mountable filters and transferred to analysis vials for analysis by gel permeation chromatography (GPC) to assess the changes in molecular weight of the polymer.

FIG. 1 illustrates the in vivo change in molecular weight of the polymers in rabbits implanted with meshes coated with (♦) poly(DTM-15-DT glutarate), (◇) poly(DTPB glutarate), (●) poly(DTMB succinate), (□) poly(DTMB glutarate), (▲) poly(DT(DATE)glutarate) and (○) poly(DTMB-10-DT succinate). Other than the control, the polymers in this study have no remaining molecular weight at times ranging from about 50 to about 180 days.

Figure 2:
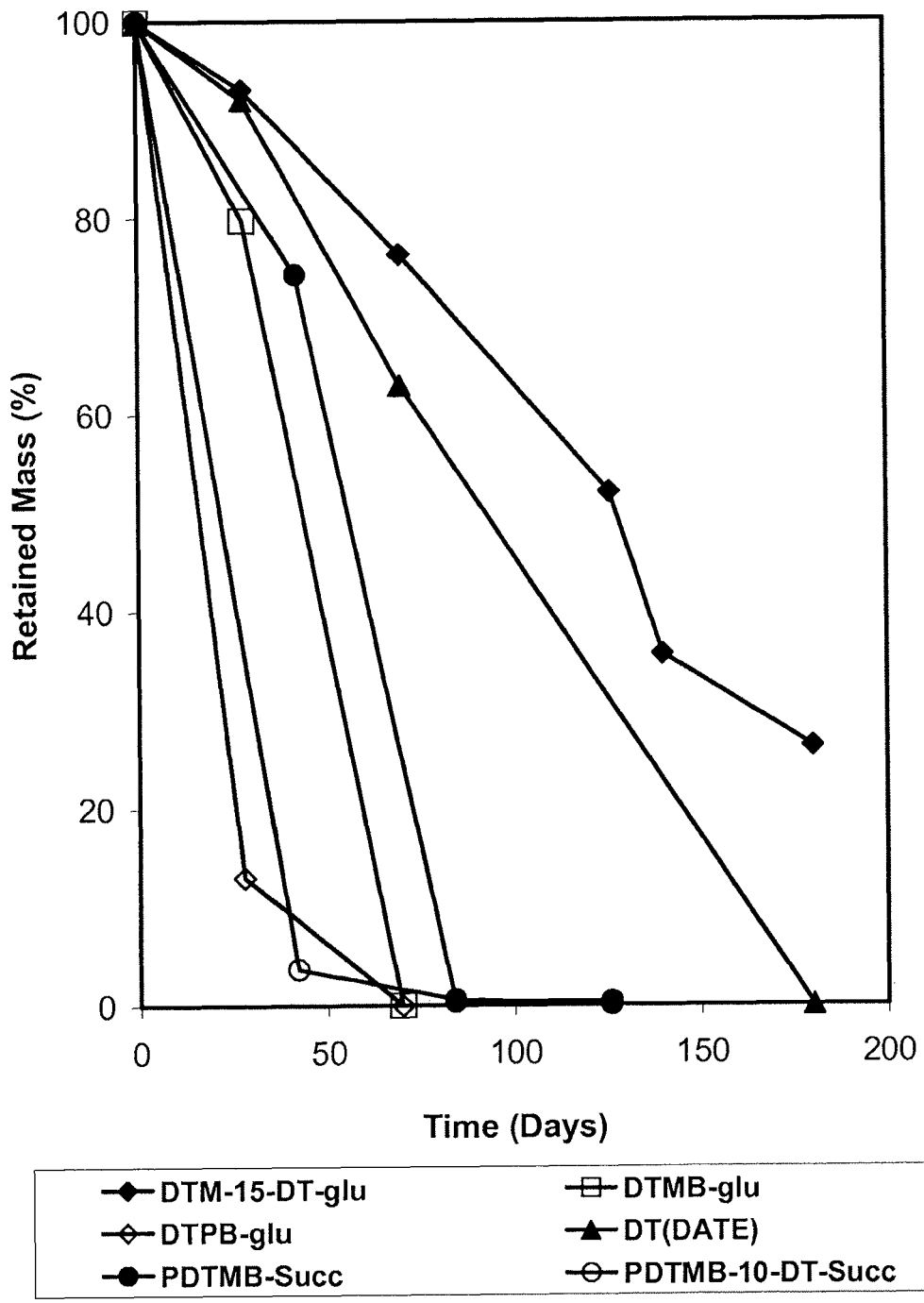
FIG. 2 graphically illustrates the mass loss from polymer coated meshes in vivo as a function of time for (♦) poly (DTM-15-DT glutarate), (◊) poly(DTPB glutarate), (●) poly(DTMB succinate), (□) poly(DTMB glutarate), (▲) poly(DT(DATE)glutarate) and (○) poly(DTMB-10-DT succinate).

To assess the mass loss profile, the coated meshes can be washed, dried and weighed (final weight) after removal from the chambers. The mass loss is determined by subtracting the final weight from the original weight of the coated mesh. FIG. 2 illustrates the mass loss during in vivo implantation in rabbits implanted with meshes coated with (♦) poly(DTM-15-DT glutarate), (◇) poly(DTPB glutarate), (●) poly (DTMB succinate), (□) poly(DTMB glutarate), (▲) poly(DT (DATE) glutarate) and (○) poly(DTMB-10-DT succinate). The polymers in this study, other than the control, show considerable mass loss by about 75 days (or earlier) in many cases. The control does not lose all of its mass during the time course of the study whereas these polymers of the invention do so.

Example 8

Drug Release

A polypropylene mesh was sonicated with acetone followed by isopropanol and dried at 50° C. overnight. The poly(DTMB-glutarate) polymer and rifampin to give a 5% loading were dissolved in a suitable solvent (tetrahydrafuran or methylene chloride). This solution was then filtered through 1 micron filter and spray coated on the mesh using Sonotek spray coater. The mesh was allowed to dry in the hood for 1 hour and then dried under vacuum at room temperature to remove all solvent.

Figure 3:
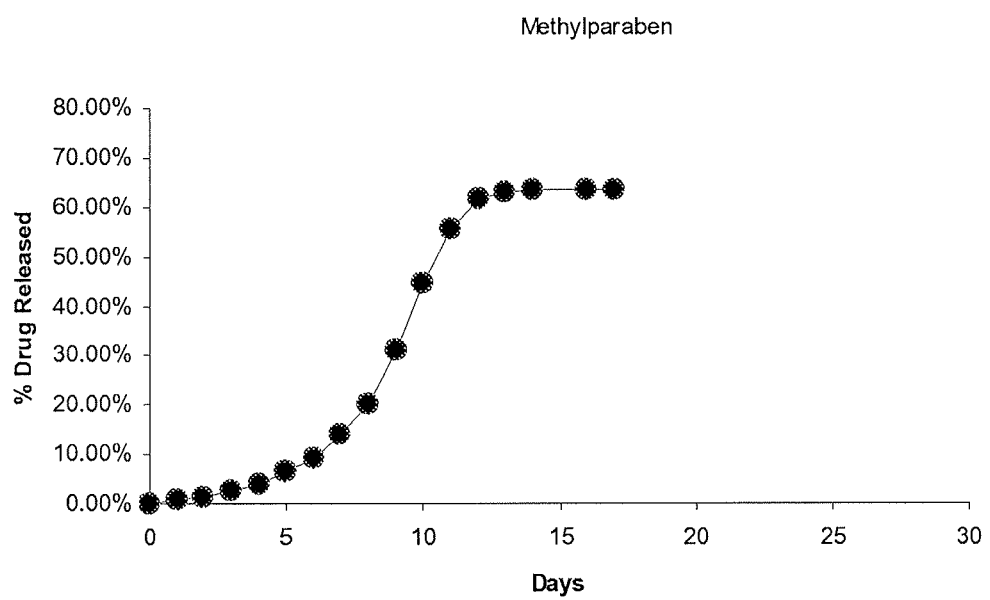
FIG. 3 shows the release profiles of rifampin from poly (DTMB glutarate) a spray-coated polypropylene mesh.

For drug release, calculated amounts of the devices (based on High Performance Liquid Chromatography sensitivity) were placed in 20 mL scintillation vials. PBS (10 mL) was added, the vials capped and placed in an incubator-shaker at 37° C. At predetermined time intervals, the buffer was pipetted out and analyzed by HPLC. The buffer was then replaced with 10 mL of fresh buffer. The kinetics of drug release was obtained by plotting the cumulative drug released against time (FIG. 3).

A poly(DTMB-glutarate) film with a 5% loading of rifampin, a 5% loading of minocycline, or both, is prepared as generally by the casting method described in U.S. Ser. No. 12/058,060, filed Mar. 28, 2008. Once dry, the films are cut into small pieces and placed into a vial containing PBS. Aliquots of buffer are removed periodically for analysis and replaced with fresh buffer. Samples are analyzed by HPLC to determine the cumulative amount of released rifampin or minocycline.

We claim:

1. A polymer comprising one or more monomer units represented by either of the formulas:

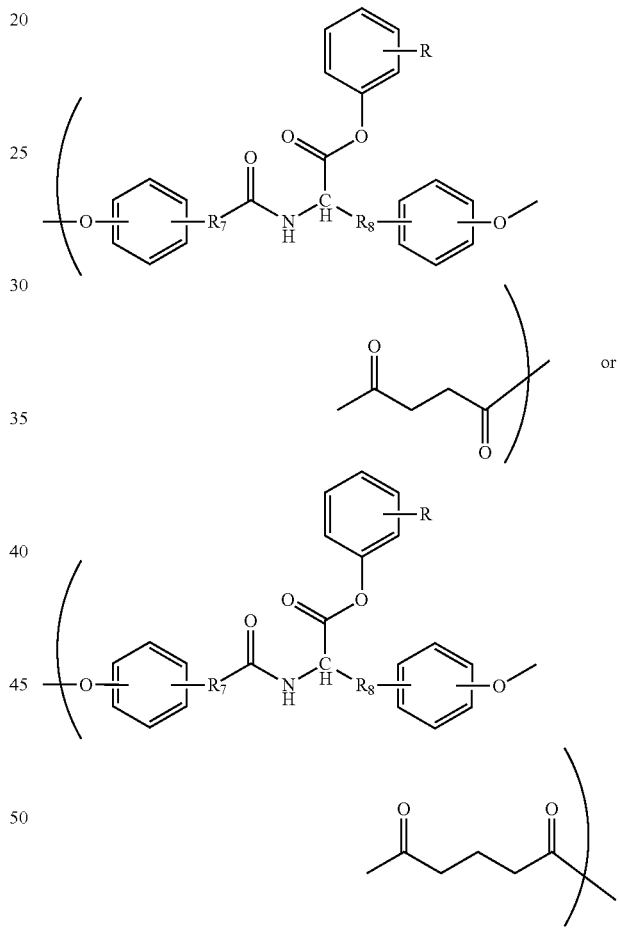

wherein from zero to five R substituents are present at any position on the phenyl ring, and each R is independently linear or branched, substituted or unsubstituted, saturated or unsaturated alkyl, aryl, alkylaryl, heteroatom-containing alkyl or aryl, alkylcycloalkyl, alkoxy, aryloxy or alkylether having from 1 to 20 carbon atoms; halide; nitro; $-(R_2)_rO((CR_3R_4)_aO)_s-R_5$; $-O((CR_3R_4)_aO)_s-R_5$; $-C(O)-R_5$; $-(R_2)_bO(O)-YR_6$; a protected hydroxyl group; a protected amino group or a protected carboxylic acid group;

Y is $-O-$ or $-NH-$;

each $R_2$ is linear or branched, lower alkylene or lower alkenylene;

each $R_3$ and $R_4$ is independently hydrogen, or linear or branched lower alkyl; each $R_5$ is independently linear or branched, substituted or unsubstituted, saturated or unsaturated alkyl;

each $R_6$ is hydrogen; saturated or unsaturated alkyl, aryl or alkylaryl having from 1 to 20 carbon atoms; or —$(R_2)_rO((CR_3R_4)_aO)_s$—$R_5$;

$R_7$ and $R_8$ are independently a bond, or linear or branched, substituted or unsubstituted alkyl, alkenyl or alkynyl having from 1 to 20 carbon atoms, each a is independently 1 to 4; each b is independently zero or one; each r is independently 1 to 4; each s is independently 1 to 5000.

2. The polymer of claim 1, where said monomer is represented by the formula:

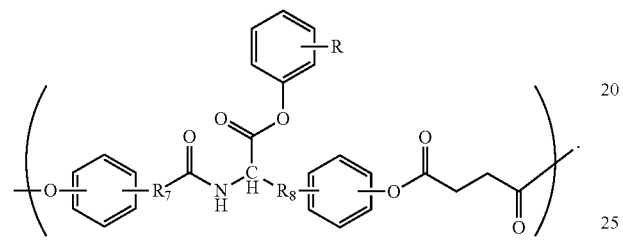

3. The polymner of claim 2, wherein $R_7$ is —$CH_2$—$CH_2$— and $R_8$ is —$CH_2$—.

4. The polymer of claim 3, wherein said monomer is represented by the formula:

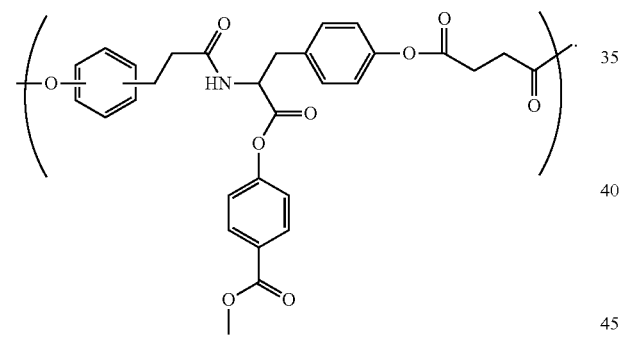

5. The polymer of claim 3, wherein said monomer is represented by the formula:

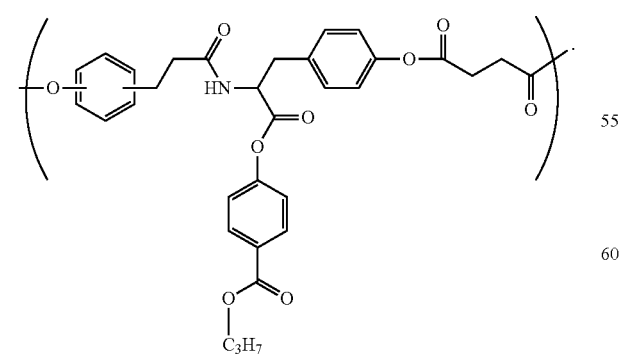

6. The polymer of claim 2, wherein $R_7$ is a bond and $R_8$ is —$CH_2$—.

7. The polymer of claim 6, wherein said monomer is represented by the formula:

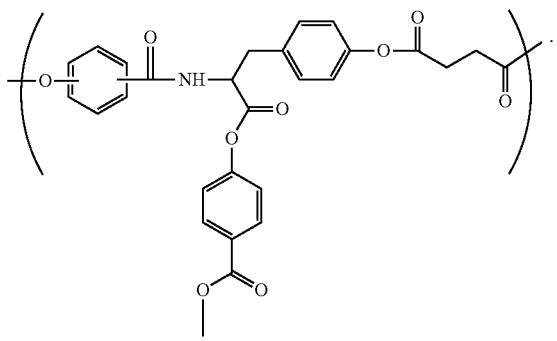

8. The polymer of claim 6, wherein said monomer is represented by the formula:

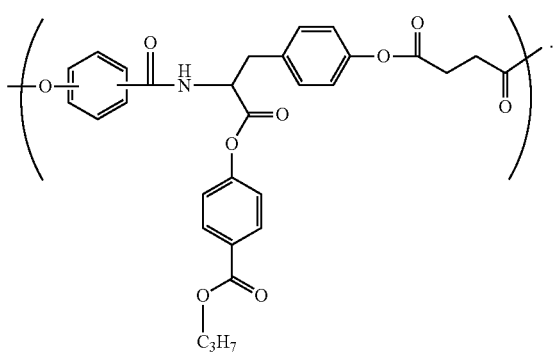

9. The polymer of claim 1, where said monomer is represented by the formula:

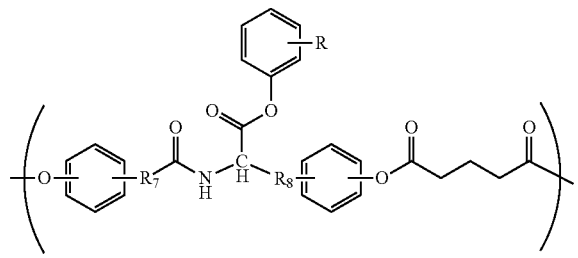

10. The polymer of claim 9, wherein $R_7$ is —$CH_2$—$CH_2$— and $R_8$ is —$CH_2$—.

11. The polymer of claim 10, wherein said monomer is represented by the formula:

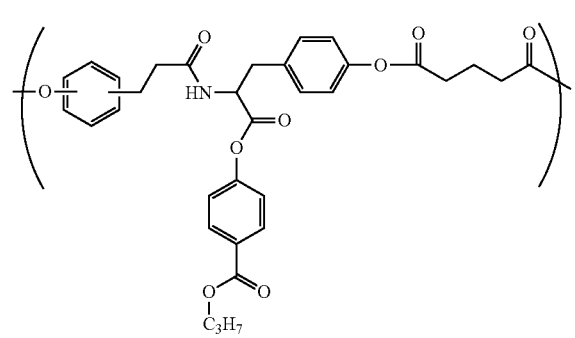

12. The polymer of claim 9, wherein $R_7$ is a bond and $R_8$ is —$CH_2$—.
13. The polymer of claim 12, wherein said monomer is represented by the formula:
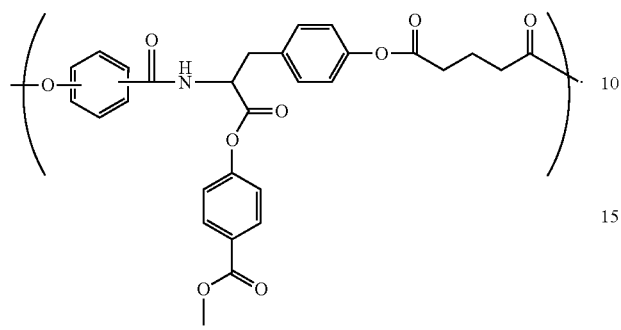
14. The polymer of claim 10, wherein said monomer is represented by the formula:
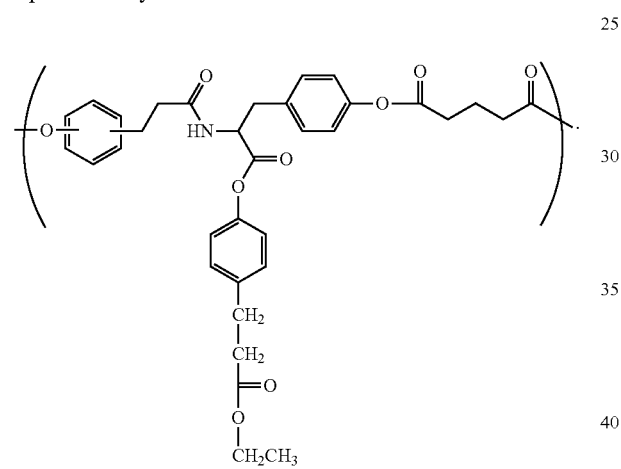
15. The polymer of claim 3, wherein said monomer is represented by the formula:
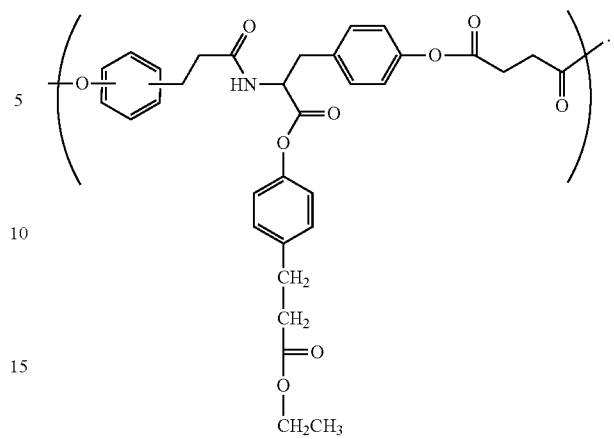
16. The polymer of claim 10, wherein said monomer is represented by the formula:
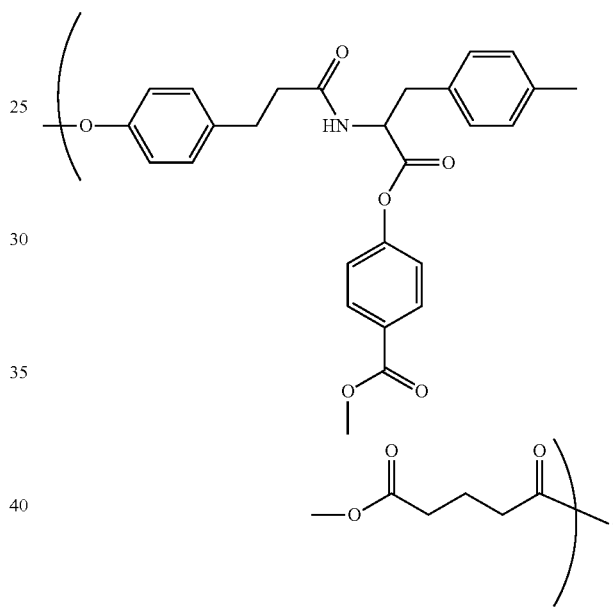
* * * * *